United States Patent
Tanaka et al.

(10) Patent No.: US 10,959,602 B2
(45) Date of Patent: Mar. 30, 2021

(54) ANTENNA HOLDER AND ANTENNA ATTACHMENT PORTION

(71) Applicant: OLYMPUS CORPORATION, Tokyo (JP)

(72) Inventors: Yuya Tanaka, Tokyo (JP); Hironao Kawano, Machida (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 16/559,747

(22) Filed: Sep. 4, 2019

(65) Prior Publication Data
US 2019/0387957 A1    Dec. 26, 2019

Related U.S. Application Data

(63) Continuation of application No. PCT/JP2017/036737, filed on Oct. 11, 2017.

(30) Foreign Application Priority Data

Mar. 24, 2017    (JP) .............................. JP2017-059869

(51) Int. Cl.
*H01Q 1/38* (2006.01)
*A61B 1/00* (2006.01)
(Continued)

(52) U.S. Cl.
CPC ......... *A61B 1/00016* (2013.01); *H01Q 1/273* (2013.01); *H01Q 1/38* (2013.01);
(Continued)

(58) Field of Classification Search
CPC ........... H01Q 1/273; H01Q 1/38; H01Q 21/29
See application file for complete search history.

(56) References Cited

U.S. PATENT DOCUMENTS

2013/0178702 A1    7/2013    Tanaka
2016/0309984 A1    10/2016   Tanaka

FOREIGN PATENT DOCUMENTS

| JP | 2005-245938 A | 9/2005 |
| JP | 2016-054924 A | 4/2016 |
(Continued)

OTHER PUBLICATIONS

International Search Report dated Nov. 28, 2017 issued in PCT/JP2017/036737.
(Continued)

*Primary Examiner* — Graham P Smith
(74) *Attorney, Agent, or Firm* — Scully, Scott, Murphy & Presser, P.C.

(57) ABSTRACT

An antenna holder includes: an antenna attachment portion attached with a plurality of receiving antennas configured to receive wireless signals transmitted from a medical device introduced into a subject; and a fitting portion where the antenna attachment portion is detachably attached and that is fitted on the subject. The antenna attachment portion includes: a plurality of antenna fixing portions where at least one of positions of the plurality of receiving antennas is fixed; an interlinking portion configured to variably interlink relative positions of the plurality of antenna fixing portions; and a first attachment portion attached to the fitting portion. The fitting portion includes: a second attachment portion where the first attachment portion is detachably attached, the second attachment portion being configured to determine positions of the plurality of antenna fixing portions upon fitting of the plurality of antenna fixing portions on the subject, according to build of the subject.

13 Claims, 40 Drawing Sheets

(51) Int. Cl.
*H01Q 1/27* (2006.01)
*H01Q 21/29* (2006.01)
*A61B 1/04* (2006.01)

(52) U.S. Cl.
CPC .......... *H01Q 21/29* (2013.01); *A61B 1/00045* (2013.01); *A61B 1/041* (2013.01)

(56) References Cited

FOREIGN PATENT DOCUMENTS

| JP | 2016-214655 A | 12/2016 |
| WO | WO 2012/165426 A1 | 12/2012 |
| WO | WO 2016/021229 A1 | 2/2016 |

OTHER PUBLICATIONS

Japanese Office Action dated Apr. 10, 2018 issued in JP 2018-505497.

ANTENNA HOLDER AND ANTENNA ATTACHMENT PORTION

This application is a continuation of PCT International Application No. PCT/JP2017/036737 filed on Oct. 11, 2017, which designates the United States, incorporated herein by reference, and which claims the benefit of priority from Japanese Patent Application No. 2017-059869, filed on Mar. 24, 2017, incorporated herein by reference.

BACKGROUND

The present disclosure relates to an antenna holder and an antenna attachment portion included in the antenna holder.

In the field of endoscopes, known is a capsule endoscope device having an imaging function, a wireless communication function, and the like, which are built in a capsule-shaped casing formed into a size introducible into a digestive tract of a subject, such as a patient. After being swallowed from the mouth of the subject, this capsule endoscope device sequentially captures images of the interior of the subject, generates image data, and sequentially transmits the image data wirelessly, while moving through the interior of the subject, such as the digestive tract, due to the peristaltic movement or the like.

The image data thus transmitted wirelessly by the capsule endoscope device are received by a receiving device via plural receiving antennas provided outside the subject. Each of these plural receiving antennas is inserted in an antenna holder, and fixed to a body surface of the subject. For example, a technique for fixing receiving antennas in a diagnostic jacket serving as an antenna holder is disclosed in Japanese Patent Application Laid-open No. 2005-245938.

SUMMARY

According to one aspect of the present disclosure, there is provided an antenna holder including: an antenna attachment portion attached with a plurality of receiving antennas configured to receive wireless signals transmitted from a medical device introduced into a subject; and a fitting portion where the antenna attachment portion is detachably attached and that is fitted on the subject, wherein the antenna attachment portion includes: a plurality of antenna fixing portions where at least one of positions of the plurality of receiving antennas is fixed; an interlinking portion configured to variably interlink relative positions of the plurality of antenna fixing portions; and a first attachment portion attached to the fitting portion, and the fitting portion includes: a second attachment portion where the first attachment portion is detachably attached, the second attachment portion being configured to determine positions of the plurality of antenna fixing portions upon fitting of the plurality of antenna fixing portions on the subject, according to build of the subject.

According to another aspect of the present disclosure, there is provided an antenna attachment portion attached with a plurality of receiving antennas configured to receive wireless signals transmitted from a medical device introduced into a subject, the antenna attachment portion including: a plurality of antenna fixing portions where at least one of positions of the plurality of receiving antennas is fixed; an interlinking portion configured to variably interlink relative positions of the plurality of antenna fixing portions; and a first attachment portion attached to the fitting portion.

The above and other features, advantages and technical and industrial significance of this disclosure will be better understood by reading the following detailed description of presently preferred embodiments of the disclosure, when considered in connection with the accompanying drawings.

DETAILED DESCRIPTION

Described hereinafter by reference to the drawings are embodiments of an antenna holder according to the present disclosure. The present disclosure is not limited by these embodiments. The present disclosure is applicable generally to antenna holders.

Furthermore, any elements that are the same or corresponding to each other are assigned with the same reference sign throughout the drawings, as appropriate. Moreover, it needs to be noted that the drawings are schematic, and relations among dimensions of each element, proportions among elements, and the like may be different from the actual ones. Portions having different dimensional relations and proportions among the drawings may also be included.

First Embodiment

Figure 1:
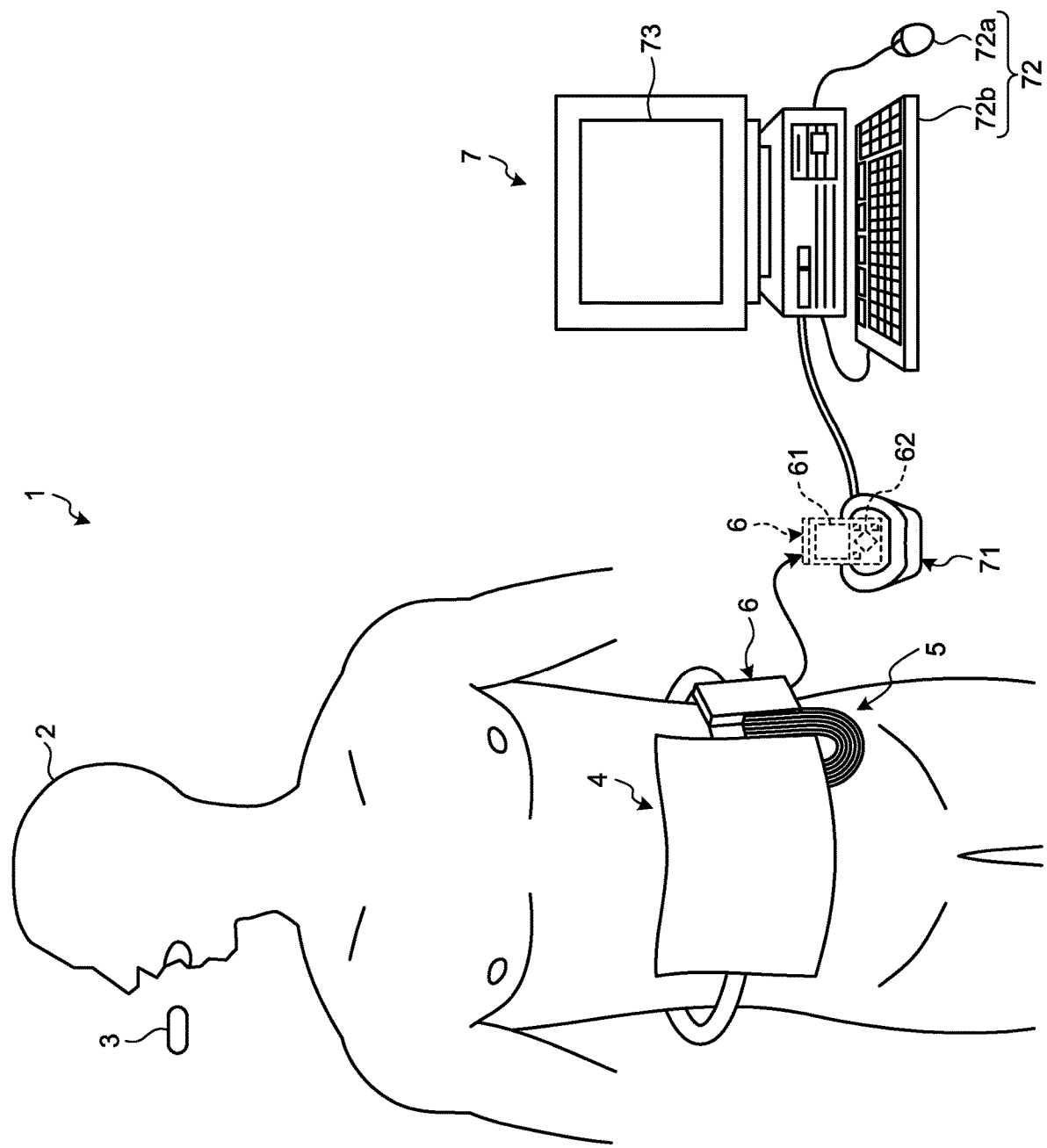
FIG. 1 is a schematic diagram illustrating a schematic configuration of a capsule endoscope system including an antenna holder according to a first embodiment.

FIG. 1 is a schematic diagram illustrating a schematic configuration of a capsule endoscope system including an antenna holder according to a first embodiment. A capsule endoscope system 1 illustrated in FIG. 1 includes: a capsule endoscope device 3 serving as a medical device introduced into a subject 2; an antenna holder 4 fitted on the subject 2; an antenna device 5 attached to the antenna holder 4 and having plural receiving antennas 51 (see FIG. 6) that receive wireless signals transmitted from the capsule endoscope device 3 introduced into the subject 2; a receiving device 6, to which the antenna device 5 is attachably and detachably connected, and which performs predetermined processing on the wireless signals received by the antenna device 5 and records or displays the processed wireless signals; and an image processing apparatus 7 that performs processing and/or display corresponding to image data on the interior of the subject 2, the image data having been captured by the capsule endoscope device 3.

The capsule endoscope device 3 has an imaging function of capturing images of the interior of the subject 2, and a wireless function of transmitting wireless signals including image data acquired by the capturing of the images of the interior of the subject 2, to the receiving antennas 51. By being swallowed into the subject 2, the capsule endoscope device 3 passes through the esophagus in the subject 2 and moves in the body cavity of the subject 2 due to the peristaltic movement of the lumen of the digestive tract. While moving in the body cavity of the subject 2, the capsule endoscope device 3 successively captures images of the interior of the body cavity of the subject 2 at minute time intervals, for example, 0.5-second intervals (for example, 2 fps), generates image data on the image-captured interior of the subject 2, and sequentially transmits the image data to the antenna device 5.

Figure 2:
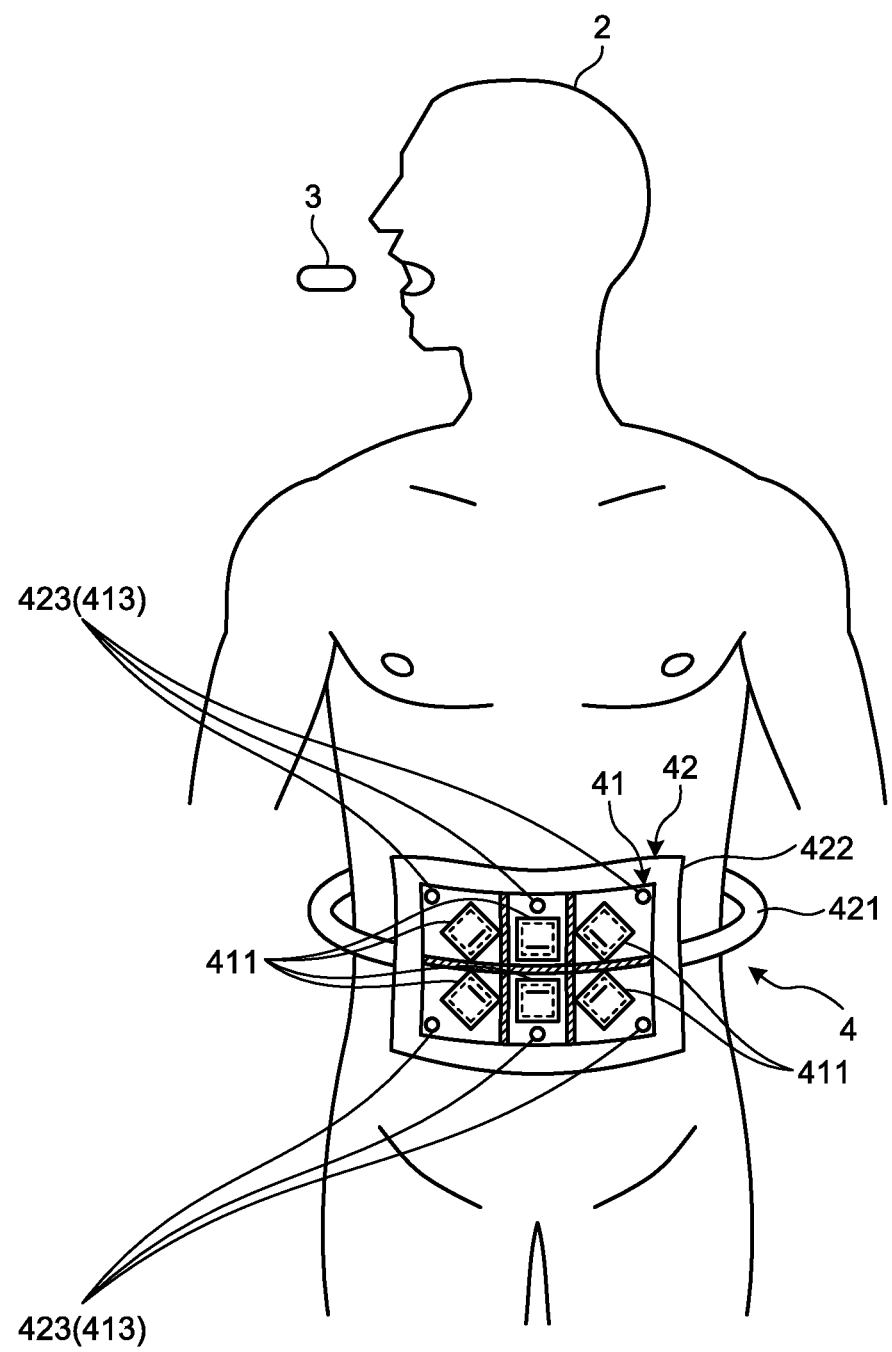
FIG. 2 is a schematic diagram illustrating a schematic configuration of the antenna holder illustrated in FIG. 1.

FIG. 2 is a schematic diagram illustrating a schematic configuration of the antenna holder illustrated in FIG. 1. As illustrated in FIG. 2, the antenna holder 4 includes: an antenna attachment portion 41, to which the plural receiving antennas 51 are attached; and a fitting portion 42, to which the antenna attachment portion 41 is attachably and detachably attached, and which is fitted on the subject 2. FIG. 2 is a diagram illustrating how the antenna holder 4 is fitted on the subject 2 having normal build; and position fixing portions 423 position antenna fixing portions 411 such that the receiving antennas 51 are positioned at appropriate positions in a waist circumference direction and a body length direction relatively to the subject 2 having normal build. Furthermore, the antenna holder 4 includes a fitting portion that positions the antenna fixing portions 411 such that the receiving antennas 51 are positioned at appropriate positions in a waist circumference direction and a body length direction relatively to a subject having obese build described later.

Figure 3:
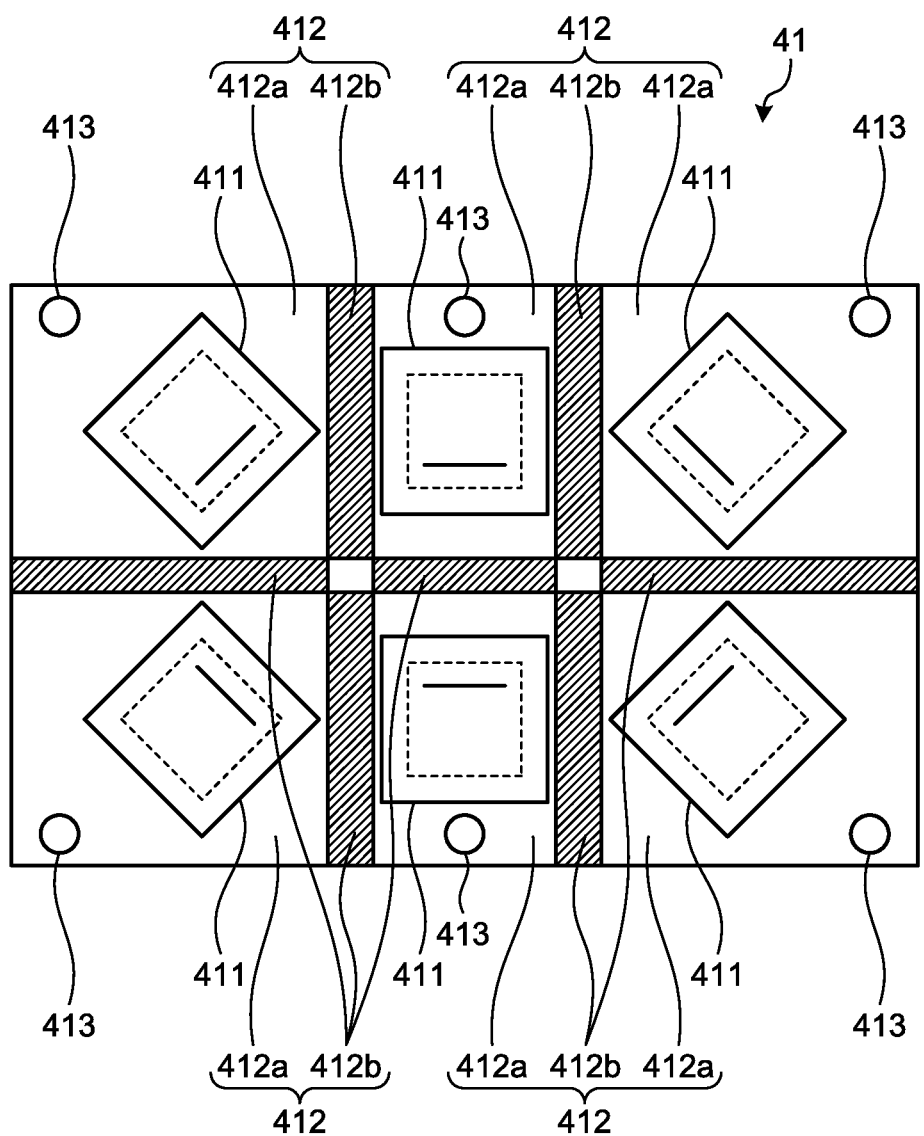
FIG. 3 is an enlarged view of an antenna attachment portion in FIG. 2.

FIG. 3 is an enlarged view of the antenna attachment portion in FIG. 2. As illustrated in FIG. 3, the antenna attachment portion 41 has six of the antenna fixing portions 411 that each fix a position of one of the receiving antennas 51, an interlinking portion 412 that variably interlinks relative positions of the antenna fixing portions 411, and attachment portions 413 serving as first attachment portions attached to the fitting portion 42. Hereinafter, for simplification of the description, the number of the antenna fixing portions 411 is described to be six, but the number of the receiving antennas 51 is not necessarily six.

Each of the antenna fixing portions 411 is made of fabric or the like formed in a pocket shape, and accommodates therein one of the receiving antennas 51. However, a configuration where a single antenna fixing portion accommodates therein plural ones of the receiving antennas 51 may be adopted instead.

The interlinking portion 412 has interlinked surfaces 412a where the antenna fixing portions 411 and the attachment portions 413 are arranged, and expanding and contracting portions 412b that expand and contract in the waist circumference direction and the body length direction of the subject 2. The expanding and contracting portions 412b are made of a material having expanding and contracting properties, such as rubber or polyurethane elastic fiber.

The attachment portions 413 are, for example, buttons or hooks, and are attached to the fitting portion 42.

As illustrated in FIG. 2, the fitting portion 42 includes a belt portion 421 fitted on the subject 2, an attached surface 422 where the antenna attachment portion 41 is attached, and the position fixing portions 423 serving as second attachment portions, each of the position fixing portions 423 being attached with one of the attachment portions 413, the position fixing portions 423 fixing positions of the plural antenna fixing portions 411 that have been fitted on the subject 2 in their positioned state, the positions being relative to the subject 2.

The belt portion 421 fixes the antenna holder 4 to be along a body surface of the subject 2, by being fitted on the subject 2.

The attached surface 422 is made of a material, such as fabric, and is deformed to be along the body surface of the subject 2 in a state where the antenna holder 4 has been fitted on the subject 2. However, the attached surface 422 is preferably prevented from being bent by expanding and contracting force of the expanding and contracting portions 412b, and preferably, is formed of a material having sufficient strength, or has therein a rigid frame or the like.

The position fixing portions 423 are buttons, hooks, or the like, which serve as counterparts of the attachment portions 413, and the attachment portions 413 are attachably and detachably fixed to the position fixing portions 423.

Figure 4:
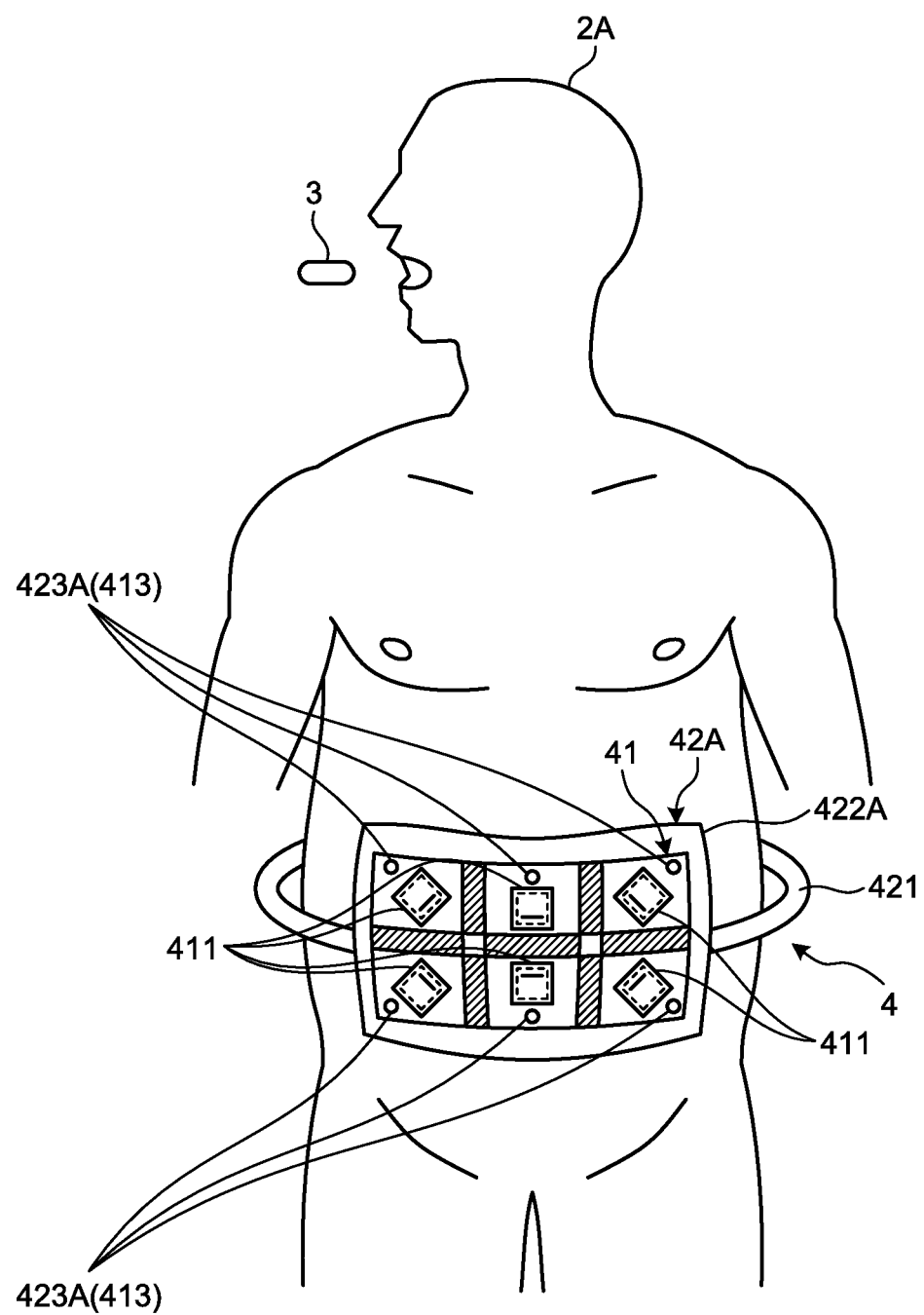
FIG. 4 is a diagram illustrating how the antenna holder is fitted on a subject having obese build.

FIG. 4 is a diagram illustrating how the antenna holder is fitted on a subject having obese build. As illustrated in FIG. 4, the antenna holder 4 fitted on a subject 2A having obese build includes a fitting portion 42A different from the fitting portion 42. The antenna attachment portion 41 attached to the fitting portion 42A is identical to the above described antenna attachment portion 41. An attached surface 422A of the fitting portion 42A is larger lengthwise and crosswise than the attached surface 422 of the fitting portion 42, and position fixing portions 423A serving as second attachment portions position the antenna fixing portions 411 such that the receiving antennas 51 are positioned at appropriate positions in a waist circumference direction and a body length direction relatively to the subject 2A having obese build.

Figure 5:
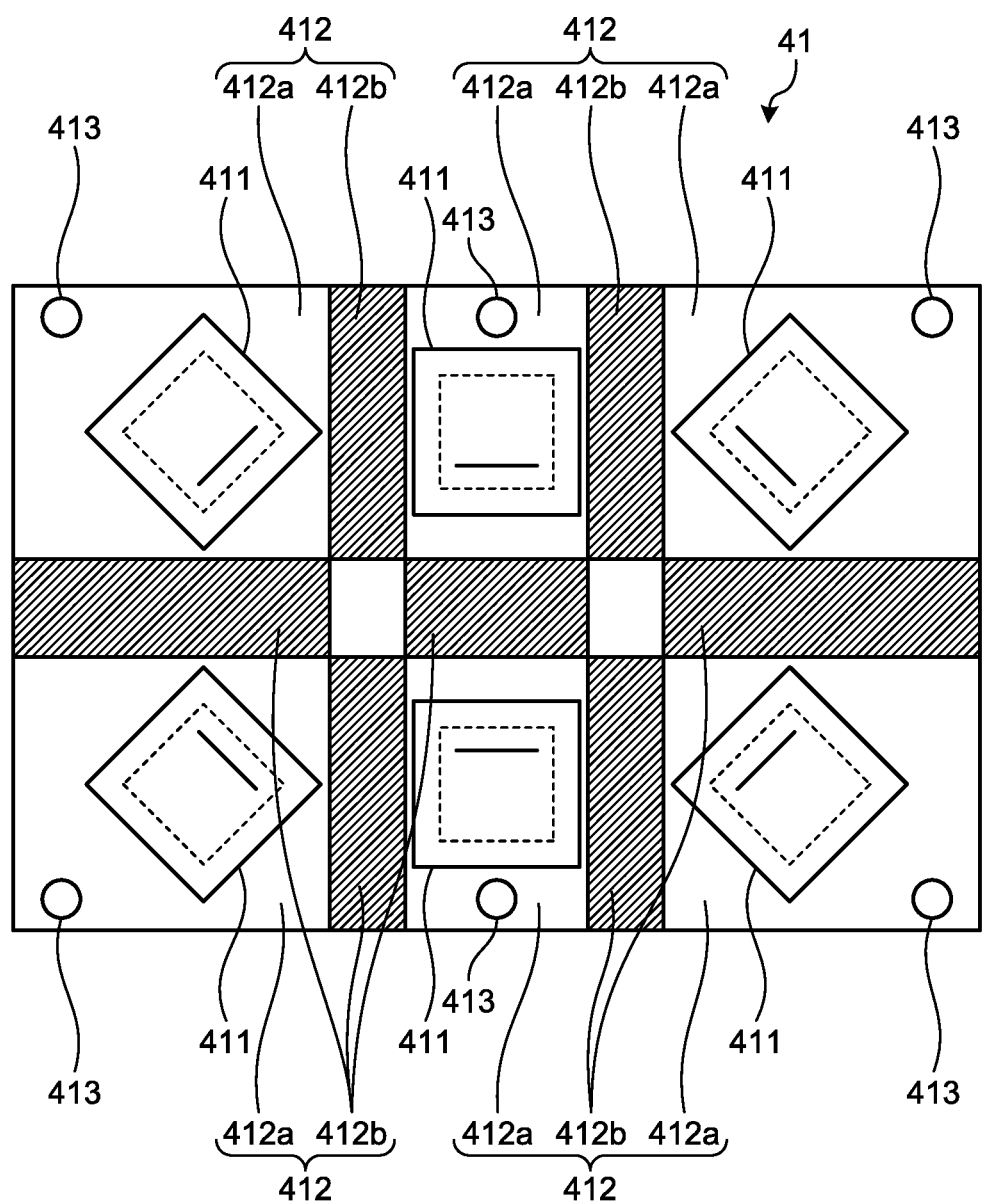
FIG. 5 is an enlarged view of the antenna attachment portion in FIG. 4.

FIG. 5 is an enlarged view of the antenna attachment portion in FIG. 4. As illustrated in FIG. 5, as the attachment portions 413 are attached to the position fixing portions 423A of the fitting portion 42A, the expanding and contracting portions 412b are brought into a state of being expanded lengthwise and crosswise. That is, positions of the antenna fixing portions 411 are moved outward and the receiving antennas 51 are able to be arranged at positions suitable for the subject 2A having obese build.

Figure 6:
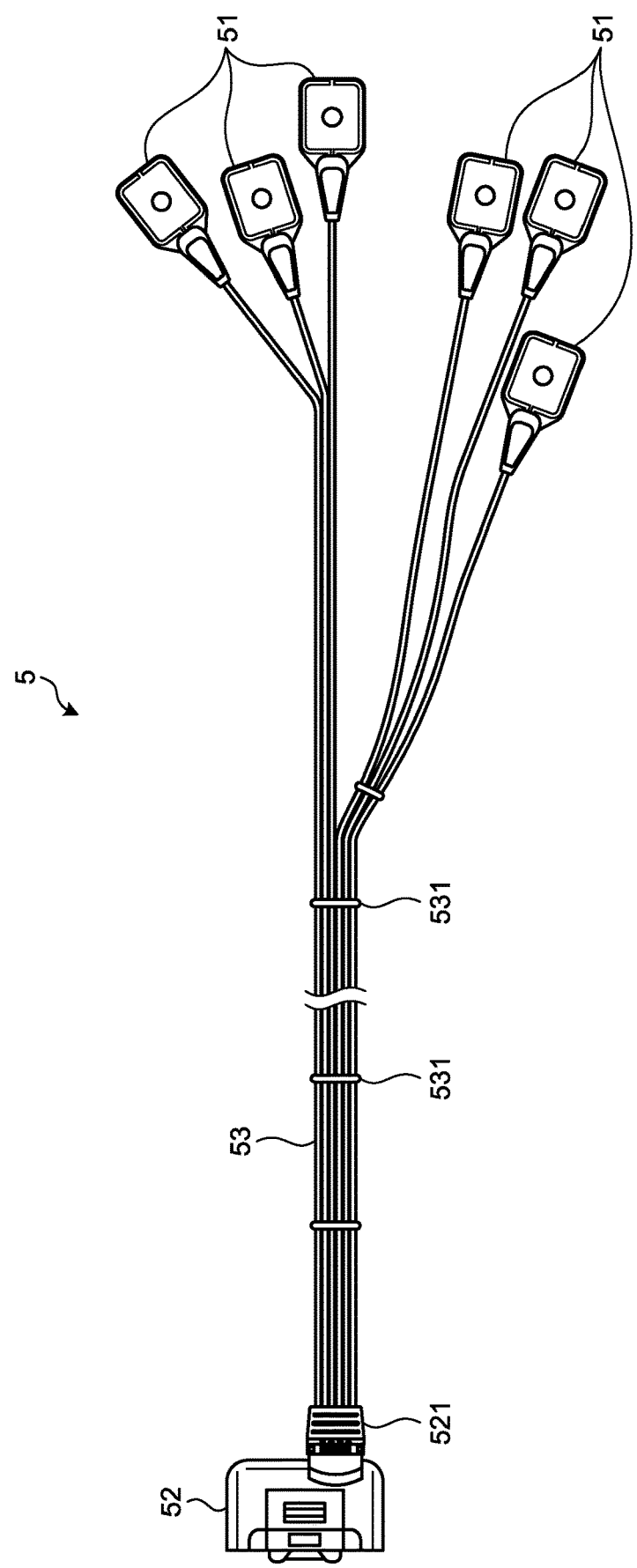
FIG. 6 is a schematic diagram illustrating a schematic configuration of receiving antennas illustrated in FIG. 1.

FIG. 6 is a schematic diagram illustrating a schematic configuration of the receiving antennas illustrated in FIG. 1. As illustrated in FIG. 6, the antenna device 5 has the plural receiving antennas 51 that receive wireless signals from the capsule endoscope device 3, and antenna cables 53, through which the wireless signals received by the plural receiving antennas 51 are propagated to the receiving device 6. Hereinafter, for simplification of the description, the number of the receiving antennas 51 is described to be six, but the number of the receiving antennas 51 is not necessarily six. Furthermore, the numbers of the antenna fixing portions 411 and receiving antennas 51 are not necessarily the same. A detailed configuration of the antenna device 5 will be described later.

The receiving device 6 records image data on the interior of the subject 2, the image data being included in the wireless signals transmitted from the capsule endoscope device 3 via the plural receiving antennas 51, or displays images corresponding to the image data on the interior of the subject 2. The receiving device 6 includes a receiving display unit 61 that displays the images corresponding to the image data, and an operating unit 62 that receives input of an instruction signal for operating the receiving device 6 and information related to positions of the receiving antennas 51. Furthermore, the receiving device 6 receives the wireless signals transmitted from the capsule endoscope device 3 via the receiving antennas 51, calculates and record, for each of the receiving antennas 51, received intensity (received field strength) of the received wireless signals, and estimates a position of the capsule endoscope device 3 in the subject 2. The receiving device 6 records, in association with one another: image data included in the wireless signals received from the capsule endoscope device 3; the received intensity of the wireless signals received by the receiving antennas 51; and time information of image data generated by the capsule endoscope device 3.

The image processing apparatus 7 displays images corresponding to image data on the interior of the subject 2, the image data having been acquired via the receiving device 6. The image processing apparatus 7 has: a cradle 71 that reads image data and the like from the receiving device 6; an operation input unit 72, such as a mouse 72a and a keyboard 72b; and a display unit 73 that displays images corresponding to the image data. When the receiving device 6 is fitted in the cradle 71, the cradle 71 acquires image data from the receiving device 6, received intensity of the receiving antennas 51 associated with the image data, time information of the image data generated by the capsule endoscope device 3, identification information of the capsule endoscope device 3, and the like, and transfers these various types of information acquired, to the image processing apparatus 7. The operation input unit 72 receives input by a user. While operating the operation input unit 72 and looking at images of the interior of the subject 2 sequentially displayed by the image processing apparatus 7, the user observes parts of a living body inside the subject 2, for example, the esophagus, the stomach, the small intestine, and the large intestine, and makes a diagnosis for the subject 2.

As described above, according to the first embodiment: the antenna holder 4 includes plural fitting portions (the fitting portion 42 and the fitting portion 42A); and plural position fixing portions (the position fixing portions 423 and the position fixing portions 423A), which are respectively included in the plural fitting portions, fix, relatively to subjects, positions of the plural antenna fixing portions 411, which have been fitted on the subjects, in a state where the positions have been positioned at positions, which have been determined beforehand according to build of the subjects and are different from one another. As a result, according to the first embodiment, the receiving antennas 51 are able to be attached at appropriate positions according to build of a subject. According to the first embodiment, positions of the antenna fixing portions 411 are determined at the time of attachment of the antenna attachment portion 41 to the fitting portion 42, and thus positions of the receiving antennas 51 do not need to be adjusted after the antenna holder 4 has been fitted on a subject, and burden on a fitter and the subject is able to be reduced.

First Modification

Figure 7:
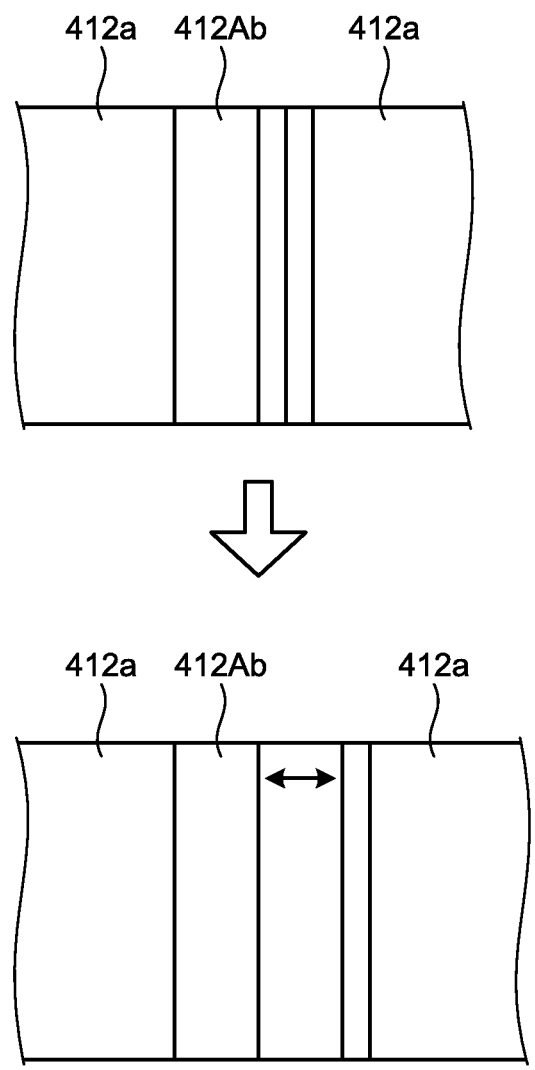
FIG. 7 is an enlarged view of a part of an expanding and contracting portion in an antenna attachment portion of an antenna holder according to a first modification.

FIG. 7 is an enlarged view of a part of an expanding and contracting portion in an antenna attachment portion of an antenna holder according to a first modification. As illustrated in FIG. 7, an expanding and contracting portion 412Ab of the antenna attachment portion according to the first modification has an accordion structure where a plate-like member is bent and connected, and expands in a left-right direction by the folded plate-like member being unfolded.

Like in this first modification, the expanding and contracting portion may be configured to have the expanding and contracting properties by means of its structure. Therefore, the expanding and contracting portion may be configured to be formed of a material not having the expanding and contracting properties.

Second Modification

Figure 8:
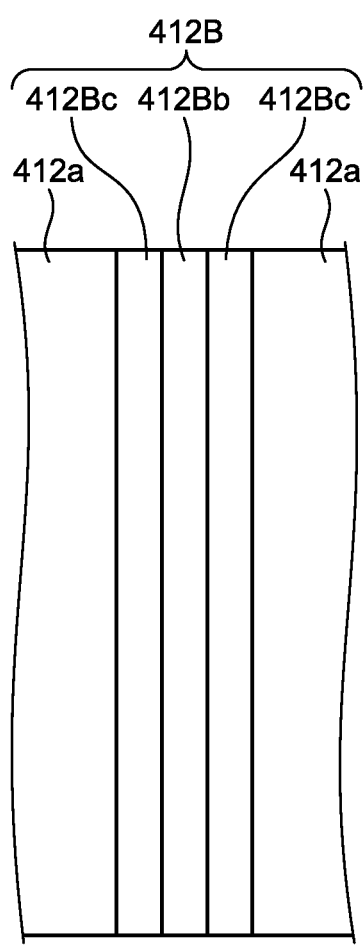
FIG. 8 is an enlarged view of a part of an expanding and contracting portion in an antenna attachment portion of an antenna holder according to a second modification.

FIG. 8 is an enlarged view of a part of an expanding and contracting portion in an antenna attachment portion of an antenna holder according to a second modification. As illustrated in FIG. 8, an interlinking portion 412B of the antenna attachment portion according to the second modification has an expanding and contracting portion 412Bb, and connecting portions 412Bc arranged on both sides of the expanding and contracting portion 412Bb. The connecting portions 412Bc are, for example, fasteners. Therefore, the interlinking portion 412B is attachable to and detachable from the antenna fixing portions 411. As a result, when the expanding and contracting portion 412Bb, which is made of, for example, rubber, deteriorates; the expanding and contracting portion 412Bb is able to be replaced by removal of the interlinking portion 412B.

Figure 9:
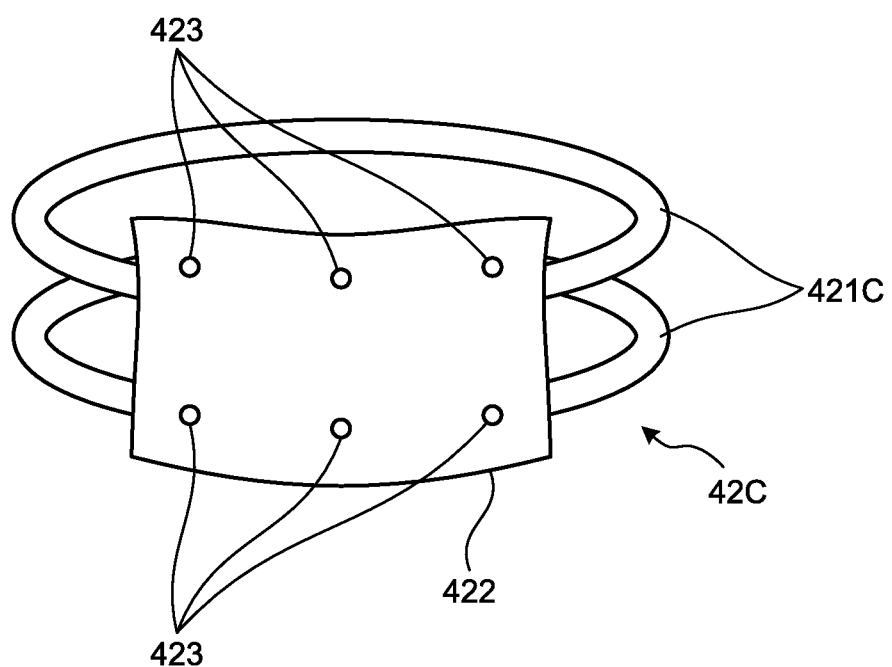
FIG. 9 is a schematic diagram illustrating a schematic configuration of a fitting portion of an antenna holder according to a third modification.

Third Modification FIG. 9 is a schematic diagram illustrating a schematic configuration of a fitting portion of an antenna holder according to a third modification. As illustrated in FIG. 9, a fitting portion 42C of the antenna holder according to the third modification has a belt portion 421C formed of two belts attached respectively to an upper portion and a lower portion of the attached surface 422.

Like in this third modification, a configuration where the number of belts in the belt portion is two or more and the antenna holder is easier to be closely attached to a subject may be adopted.

Fourth Modification

Figure 10:
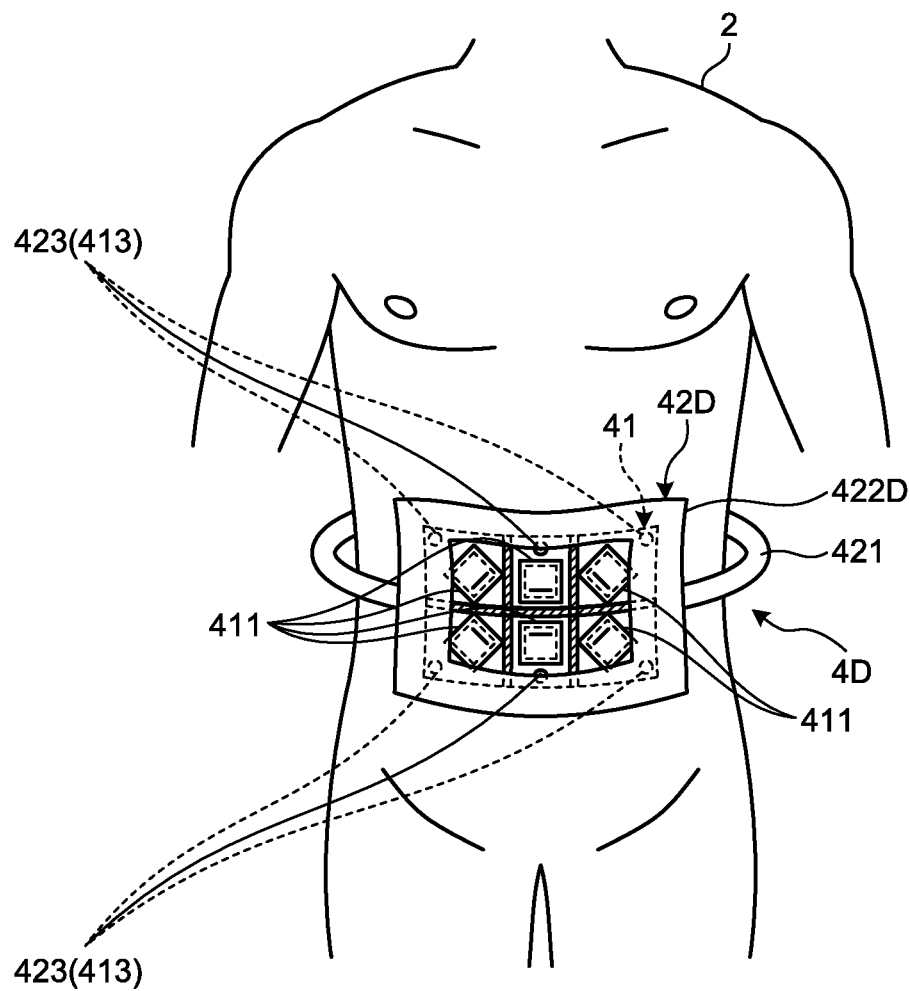
FIG. 10 is a schematic diagram illustrating a schematic configuration of an antenna holder according to a fourth modification.

FIG. 10 is a schematic diagram illustrating a schematic configuration of an antenna holder according to a fourth modification. As illustrated in FIG. 10, a fitting portion 42D of an antenna holder 4D according to the fourth modification has an attached surface 422D that is frame-shaped.

Like in this fourth modification, the shape of the attached surface is not particularly limited, and may be any shape that enables the antenna attachment portion to be attached thereto and is fittable on a subject.

Fifth Modification

Figure 11:
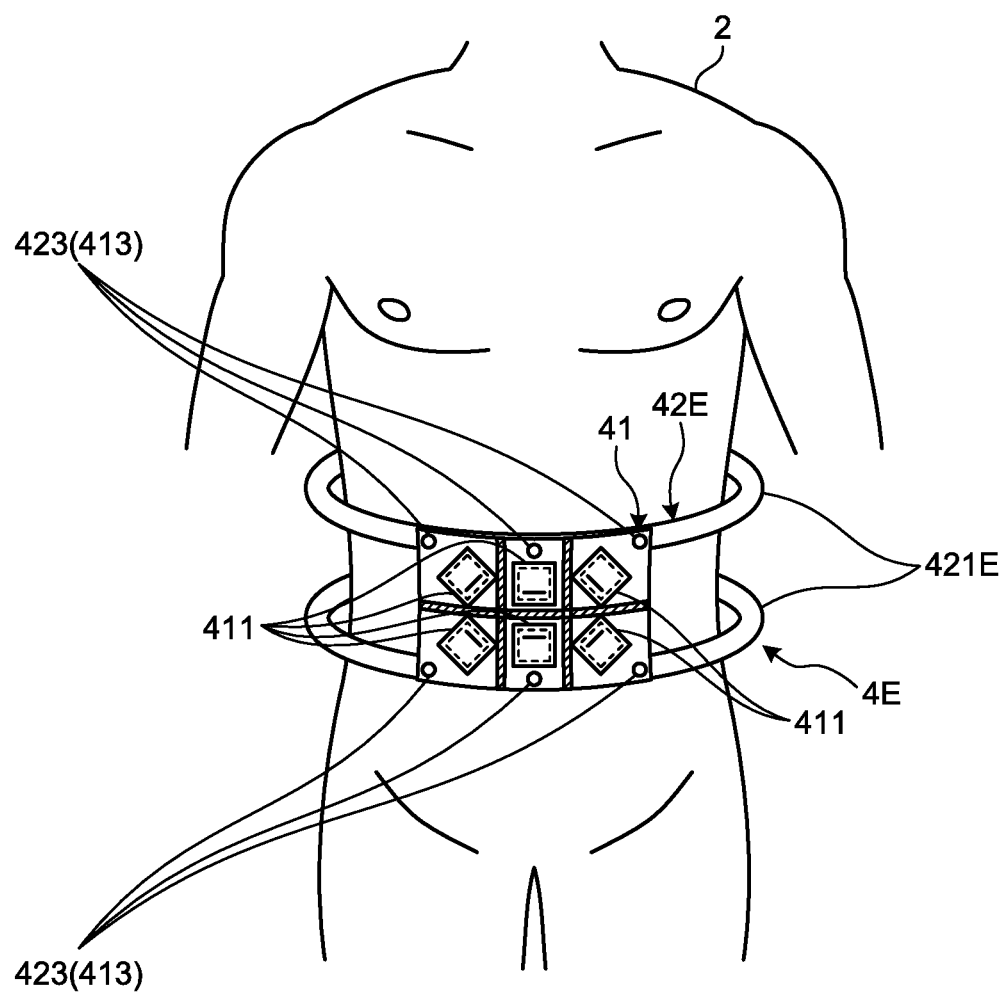
FIG. 11 is a schematic diagram illustrating a schematic configuration of an antenna holder according to a fifth modification.

FIG. 11 is a schematic diagram illustrating a schematic configuration of an antenna holder according to a fifth modification. As illustrated in FIG. 11, the position fixing portions 423 are directly arranged in a belt portion 421E formed of two belts, in a fitting portion 42E of an antenna holder 4E according to the fifth modification.

Like in this fifth modification, the fitting portion may just: enable the position fixing portions to be arranged at appropriate positions; and be fittable on a subject. Therefore, the fitting portion may be configured without an attached surface.

Sixth Modification

Figure 12:
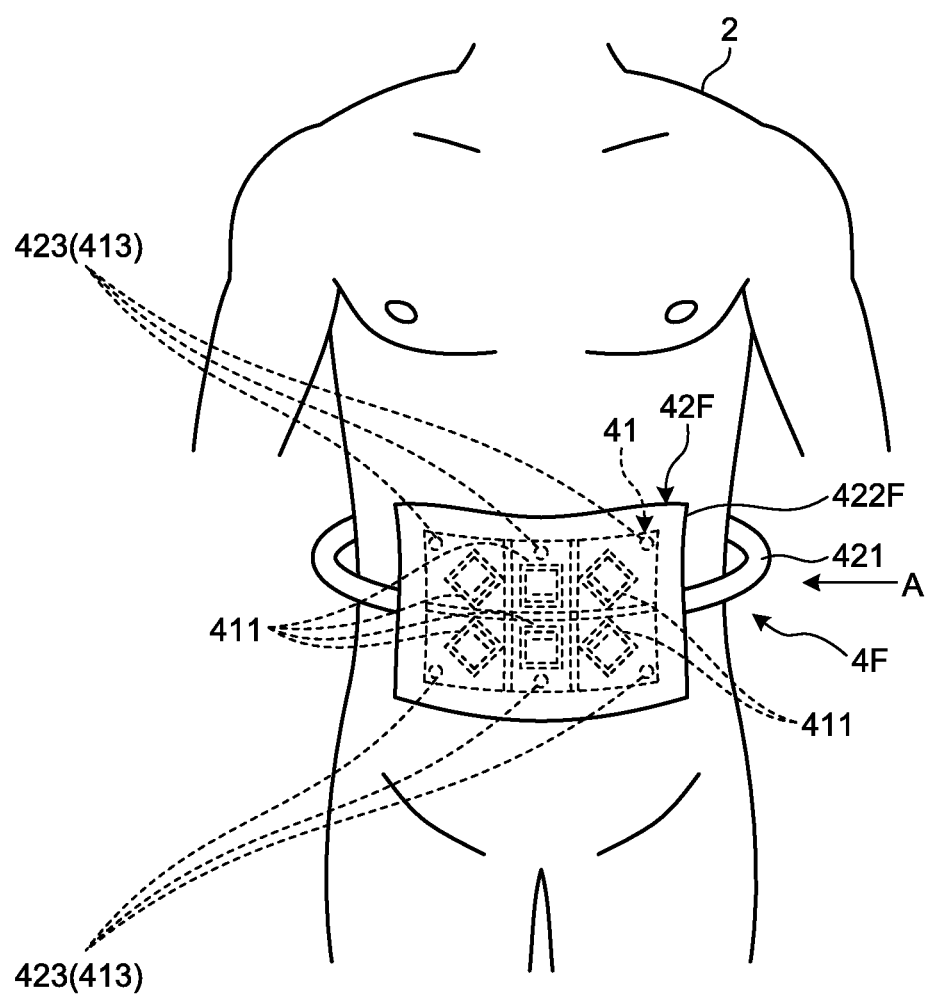
FIG. 12 is a schematic diagram illustrating a schematic configuration of an antenna holder according to a sixth modification.
Figure 13:
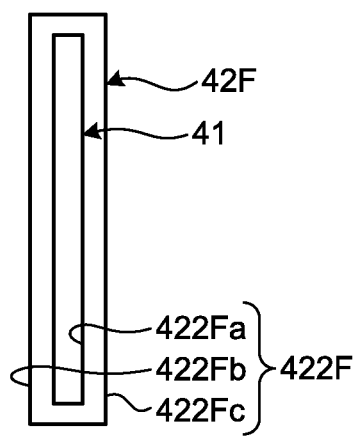
FIG. 13 is a diagram viewed in a direction of an A-arrow in FIG. 12.

FIG. 12 is a schematic diagram illustrating a schematic configuration of an antenna holder according to a sixth modification. FIG. 13 is a diagram viewed in a direction of an A-arrow in FIG. 12. As illustrated in FIG. 12 and FIG. 13, an attached surface 422F in a fitting portion 42F of an antenna holder 4F according to the sixth modification has a surface 422Fa where the position fixing portions 423 are arranged, and a surface 422Fb and a surface 422Fc that cover the antenna attachment portion 41. By the surface 422Fb and surface 422Fc covering the antenna attachment portion 41, the antenna attachment portion 41 is prevented from becoming unclean at the time of diagnosis. As a result, the trouble of cleaning the antenna attachment portion 41 every time diagnosis is made is able to be saved.

Seventh Modification

Figure 14:
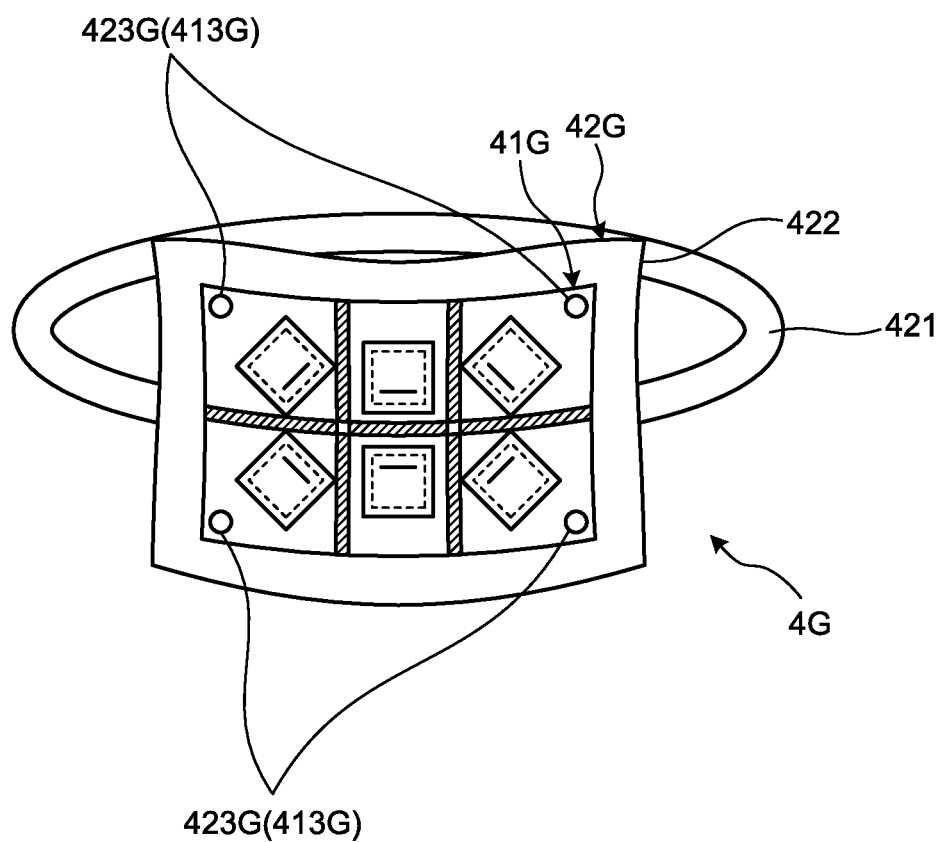
FIG. 14 is a schematic diagram illustrating a schematic configuration of an antenna holder according to a seventh modification.

FIG. 14 is a schematic diagram illustrating a schematic configuration of an antenna holder according to a seventh modification. As illustrated in FIG. 14, an antenna attachment portion 41G of an antenna holder 4G according to the seventh modification has four attachment portions 413G arranged at four corners of the antenna attachment portion 41G. Similarly, a fitting portion 42G has four position fixing portions 423G at positions corresponding to the attachment portions 413G.

Like in this seventh modification, the attachment portions may be not arranged one each for every antenna fixing portion.

Eighth Modification

Figure 15:
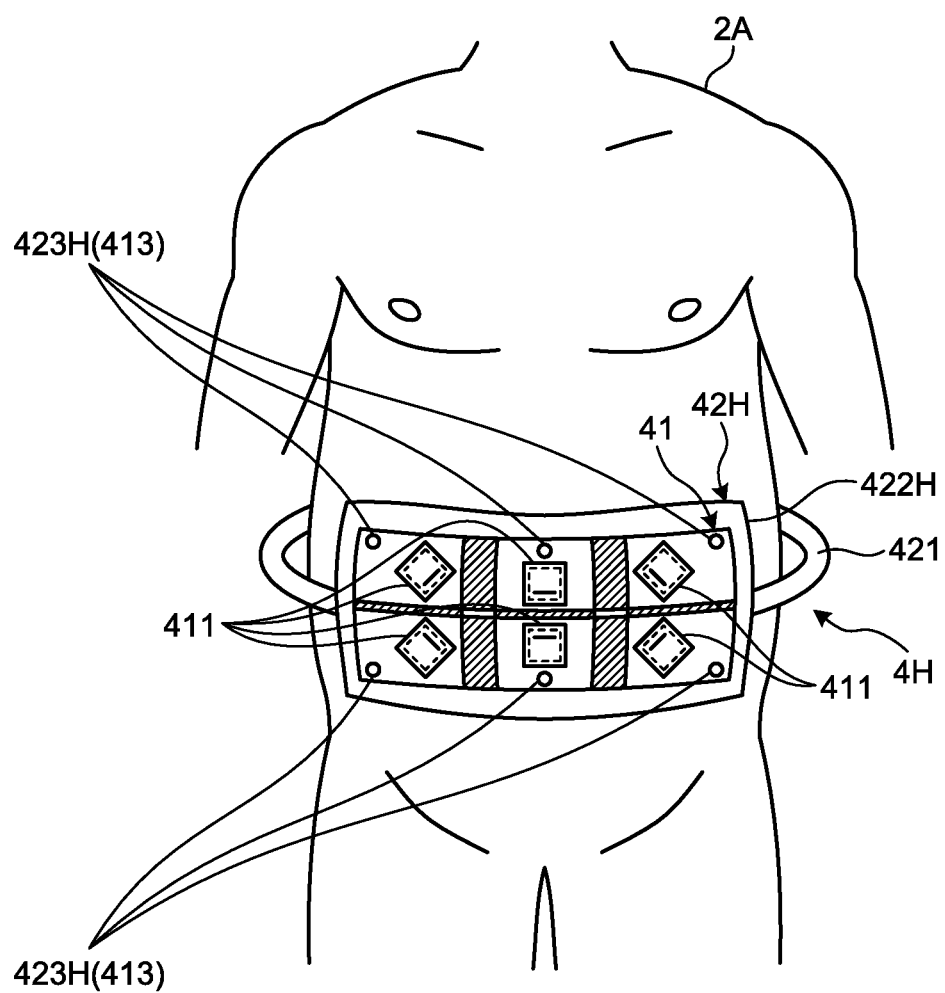
FIG. 15 is a schematic diagram illustrating a schematic configuration of an antenna holder according to an eighth modification.

FIG. 15 is a schematic diagram illustrating a schematic configuration of an antenna holder according to an eighth modification. As illustrated in FIG. 15, an antenna holder 4H is fitted on the subject 2A having obese build.

An attached surface 422H of a fitting portion 42H is larger than the attached surface 422 of the fitting portion 42 crosswise, and position fixing portions 423H of the fitting portion 42H position the antenna fixing portions 411 such that the receiving antennas 51 are positioned at appropriate positions in the waist circumference direction relatively to the subject 2A having obese build.

Figure 16:
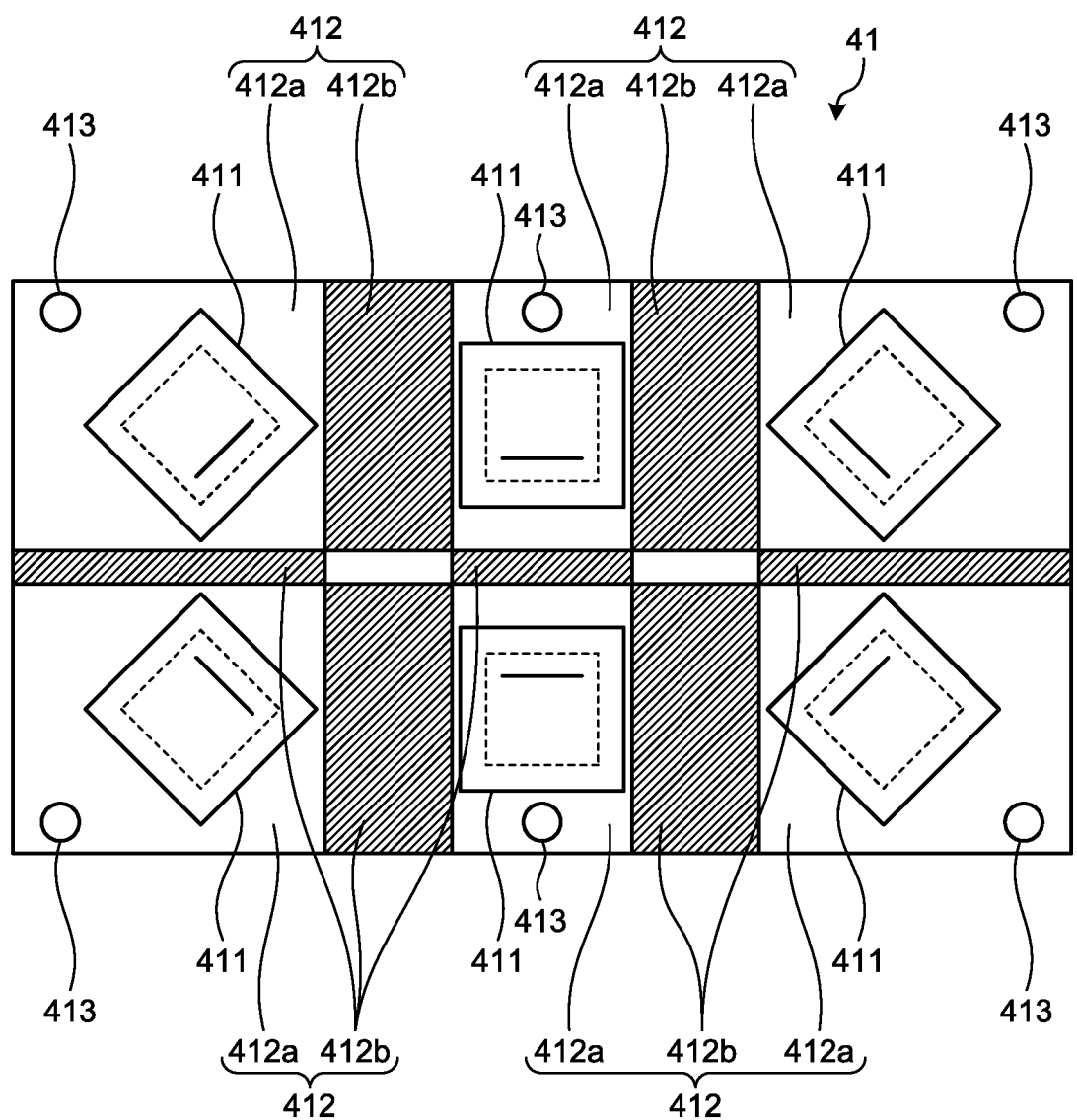
FIG. 16 is an enlarged view of an antenna attachment portion in FIG. 15.

FIG. 16 is an enlarged view of the antenna attachment portion in FIG. 15. As illustrated in FIG. 16, when the attachment portions 413 are attached to the position fixing portions 423H of the fitting portion 42H, the expanding and contracting portions 412*b* are expanded crosswise. That is, positions of the antenna fixing portions 411 are moved outward in the left-right direction, and the receiving antennas 51 are able to be arranged at positions suitable for the subject 2A having obese build.

Like in this eighth modification, the position fixing portions may position the antenna fixing portions such that the antenna fixing portions are positioned only in the waist circumference direction at appropriate positions.

Ninth Modification

Figure 17:
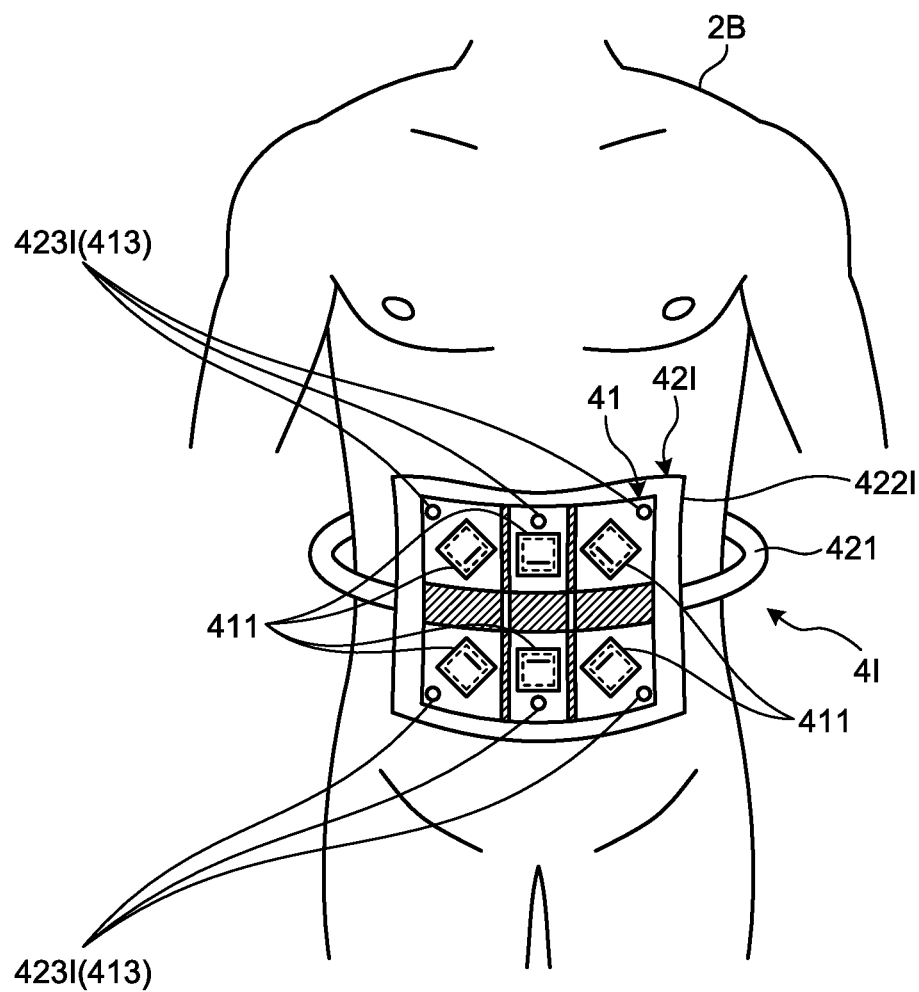
FIG. 17 is a schematic diagram illustrating a schematic configuration of an antenna holder according to a ninth modification.

FIG. 17 is a schematic diagram illustrating a schematic configuration of an antenna holder according to a ninth modification. As illustrated in FIG. 17, an antenna holder 4I is fitted on a tall subject 2B.

An attached surface 422I of a fitting portion 42I is larger than the attached surface 422 of the fitting portion 42 lengthwise, and position fixing portions 423I of the fitting portion 42I position the antenna fixing portions 411 such that the receiving antennas 51 are positioned at appropriate positions in a body length direction relatively to the tall subject 2B.

Figure 18:
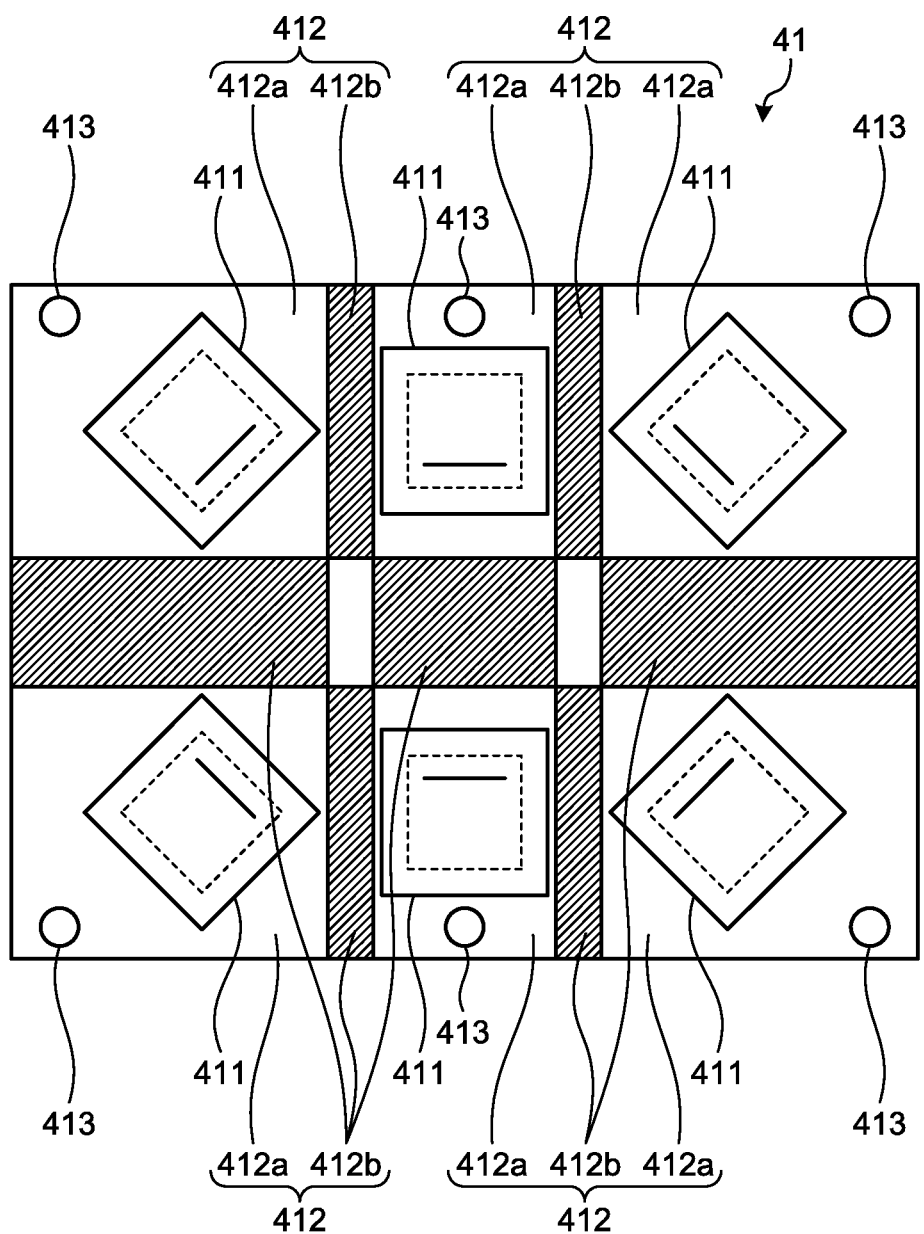
FIG. 18 is an enlarged view of an antenna attachment portion in FIG. 17.

FIG. 18 is an enlarged view of the antenna attachment portion. As illustrated in FIG. 18, when the attachment portions 413 are attached to the position fixing portions 423I of the fitting portion 42I, the expanding and contracting portions 412b are expanded lengthwise. That is, positions of the antenna fixing portions 411 are moved outward in an up-down direction, and the receiving antennas 51 are able to be arranged at positions suitable for the tall subject 2B.

Like in this ninth modification, the position fixing portions may position the antenna fixing portions such that the antenna fixing portions are positioned at appropriate positions in the body length direction only.

Second Embodiment

Described next is an antenna holder according to a second embodiment. In the following embodiments, reference signs that are the same as those according to the first embodiment will be assigned to configurations that are the same as those in the first embodiment, and description thereof will be omitted as appropriate.

Figure 19:
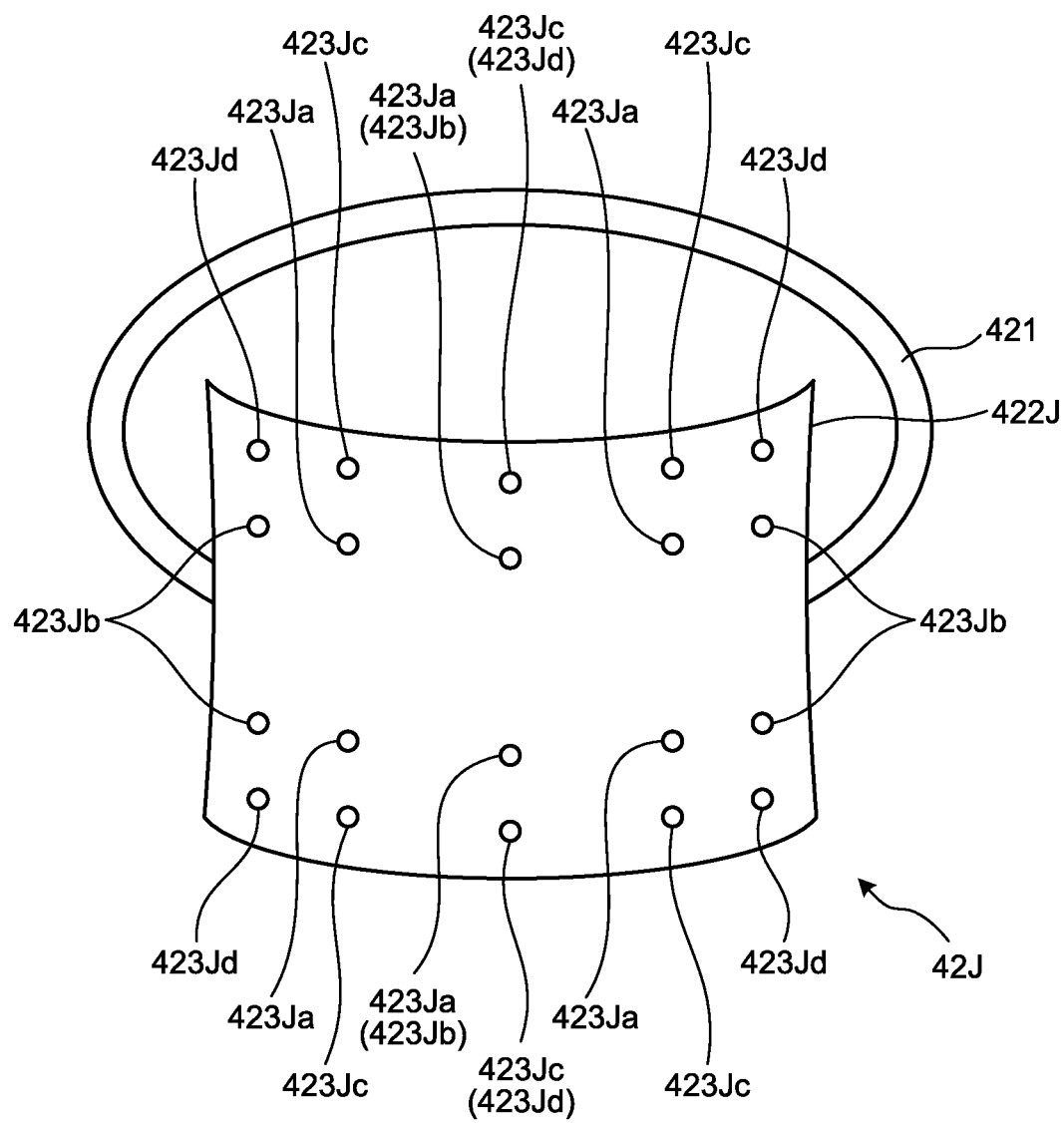
FIG. 19 is a schematic diagram illustrating a schematic configuration of a fitting portion according to a second embodiment.

FIG. 19 is a schematic diagram illustrating a schematic configuration of a fitting portion according to the second embodiment. As illustrated in FIG. 19, an attached surface 422J of a fitting portion 42J according to the second embodiment is larger lengthwise and crosswise than the attached surface 422 of the fitting portion 42, and the attached surface 422J has, arranged therein, plural position fixing portions 423Ja to 423Jd serving as second attachment portions. The plural position fixing portions 423Ja to 423Jd fix positions of the plural antenna fixing portions 411, which have been fitted on a subject, the positions being relative to the subject, in a state where the positions have been positioned at positions, which have been determined beforehand according to build of the subject and are different from one another. Like in this second embodiment, the numbers of the attachment portions and position fixing portions may be not the same.

Figure 20:
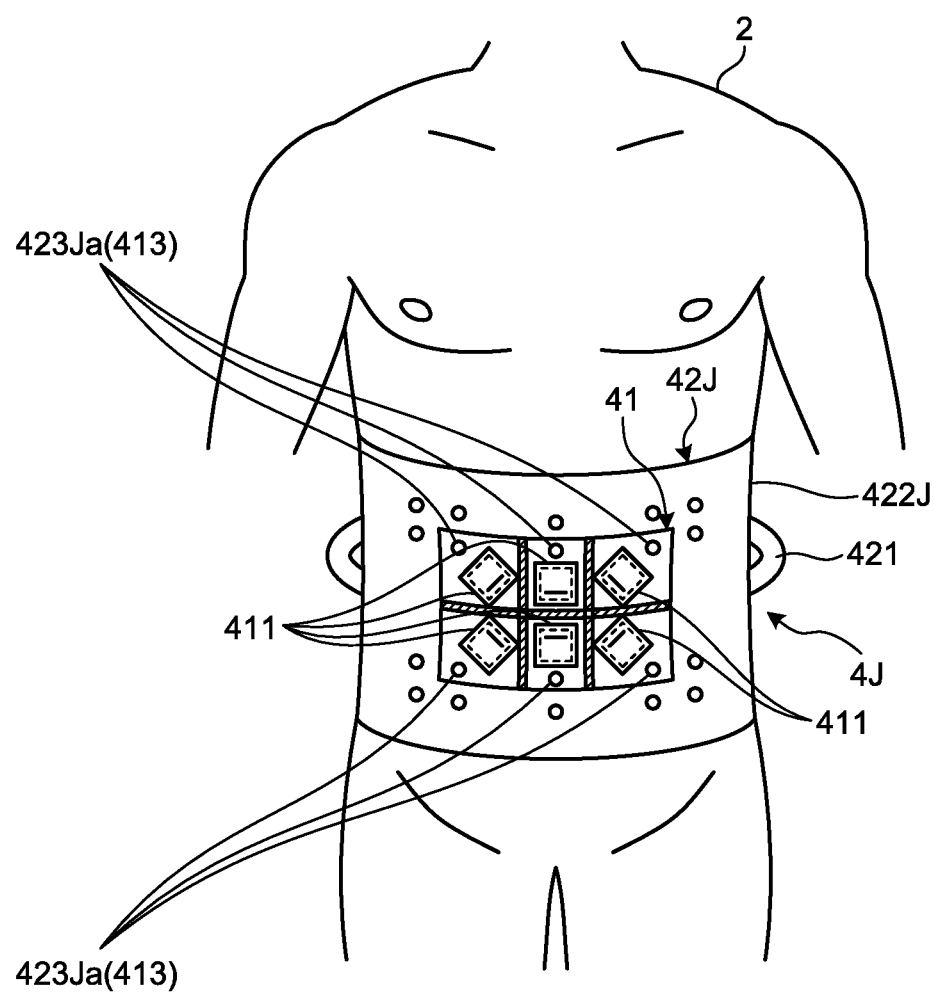
FIG. 20 is a diagram illustrating how an antenna holder according to the second embodiment is fitted on a subject having normal build.

FIG. 20 is a diagram illustrating how the antenna holder according to the second embodiment is fitted on a subject having normal build. As illustrated in FIG. 20, when the attachment portions 413 have been attached to the position fixing portions 423Ja in an antenna holder 4J, the position fixing portions 423Ja position the antenna fixing portions 411 such that the receiving antennas 51 are positioned at appropriate positions in the waist circumference direction and the body length direction, relatively to the subject 2 having normal build.

Figure 21:
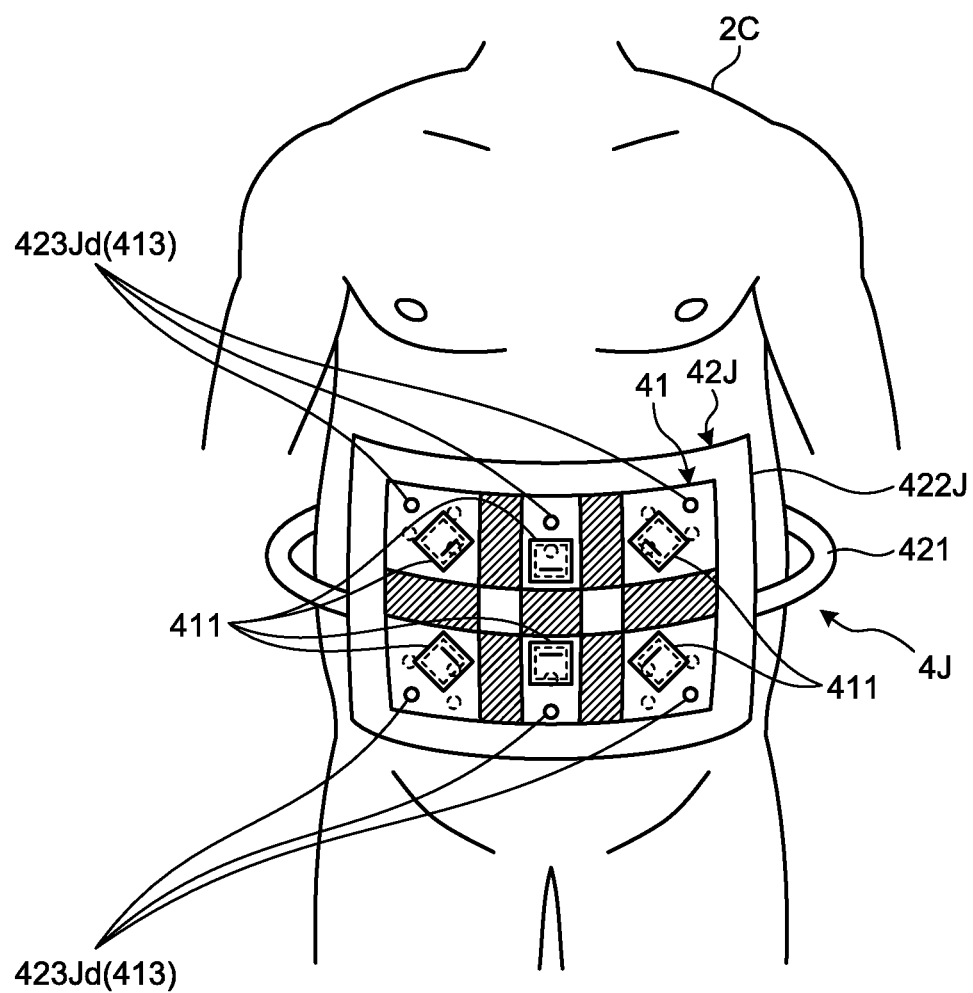
FIG. 21 is a diagram illustrating how the antenna holder according to the second embodiment is fitted on a subject having obese build.

FIG. 21 is a diagram illustrating how the antenna holder according to the second embodiment is fitted on a subject having obese build. As illustrated in FIG. 21, when the attachment portions 413 have been attached to the position fixing portions 423Jd in the antenna holder 4J, the position fixing portions 423Jd position the antenna fixing portions 411 such that the receiving antennas 51 are positioned at appropriate positions in a waist circumference direction and a body length direction, relatively to a subject 2C who has obese build and is tall.

When the attachment portions 413 have been attached to the position fixing portions 423Jb (see FIG. 19), the position fixing portions 423Jb position the antenna fixing portions 411 such that the receiving antennas 51 are arranged outside in the left-right direction and the receiving antennas 51 are positioned at appropriate positions in the waist circumference direction relatively to the subject 2A having obese build. Similarly, when the attachment portions 413 have been attached to the position fixing portions 423Jc (see FIG. 19), the position fixing portions 423Jc position the antenna fixing portions 411 such that the receiving antennas 51 are arranged outside in the up-down direction and the receiving antennas 51 are positioned at appropriate positions in the body length direction relatively to the tall subject 2B. Furthermore, at least one of colors or shapes of the position fixing portions 423Ja to 423Jd preferably differ from one another such that at the time of attachment of the attachment portions 413, identification of the position fixing portions to be attached to is facilitated.

Third Embodiment

Figure 22:
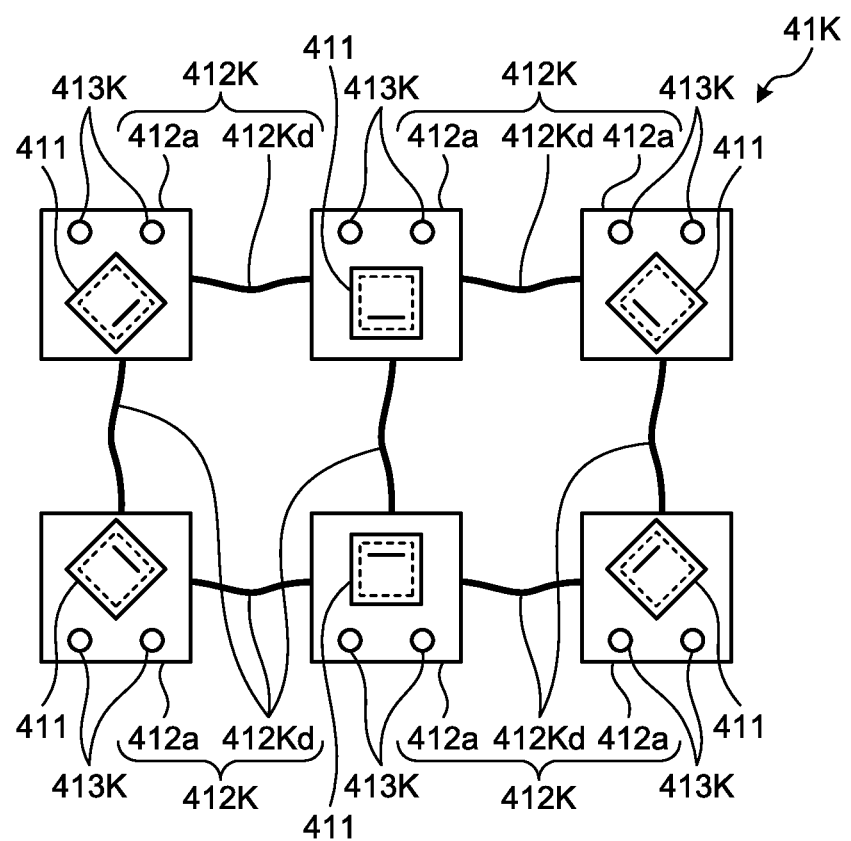
FIG. 22 is an enlarged view of an antenna attachment portion according to a third embodiment when the antenna attachment portion has been attached to the fitting portion illustrated in FIG. 2.

FIG. 22 is an enlarged view of an antenna attachment portion according to a third embodiment when the antenna attachment portion has been attached to the fitting portion illustrated in FIG. 2. As illustrated in FIG. 22, an interlinking portion 412K of an antenna attachment portion 41K according to the third embodiment has interlinked surfaces 412a, and string-like members 412Kd that variably interlink relative positions of the plural antenna fixing portions 411. Furthermore, the antenna attachment portion 41K has at least two or more attachment portions 413K arranged on each of the interlinked surfaces 412a. The fitting portion 42 illustrated in FIG. 2 positions the antenna fixing portions 411 such that the receiving antennas 51 are positioned at appropriate positions relatively to the subject 2 having normal build. In this state, the string-like members 412Kd are loose as illustrated in FIG. 22, but positions of the antenna fixing portions 411 are fixed because the attachment portions 413K are fixed to the position fixing portions 423. Furthermore, since at least two or more attachment portions 413K are arranged on each of the interlinked surfaces 412a, displacement by rotation of the antenna fixing portions 411 is prevented.

Figure 23:
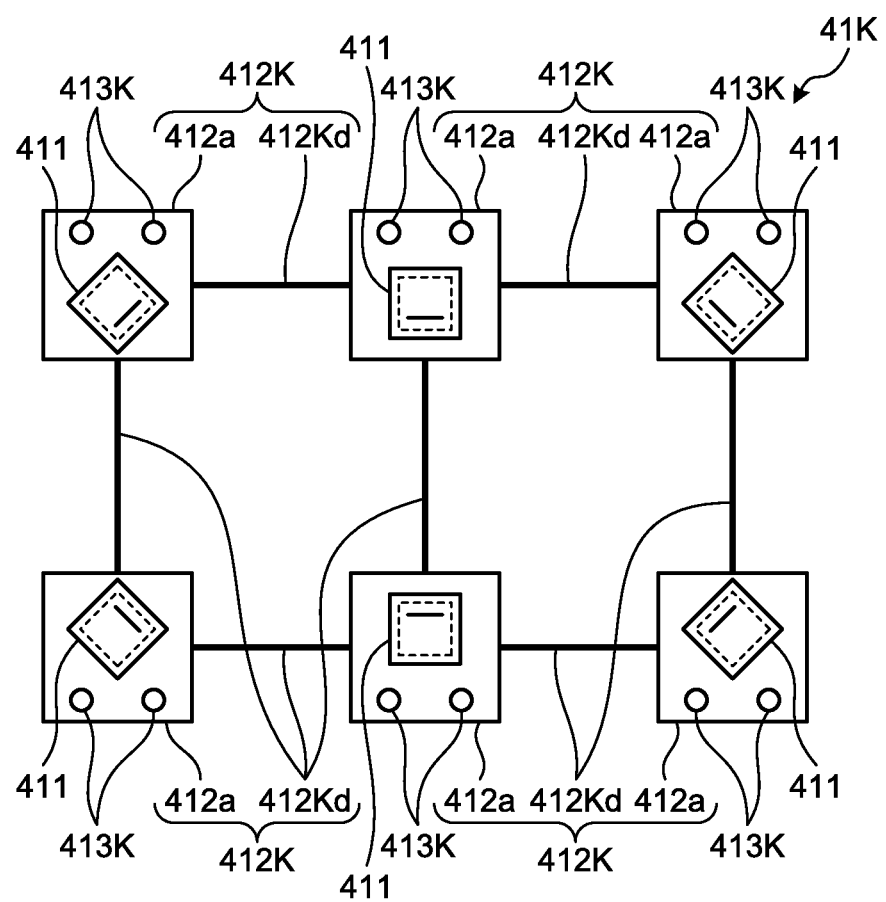
FIG. 23 is an enlarged view of the antenna attachment portion according to the third embodiment when the antenna attachment portion has been attached to the fitting portion illustrated in FIG. 4.

FIG. 23 is an enlarged view of the antenna attachment portion according to the third embodiment when the antenna attachment portion has been attached to the fitting portion illustrated in FIG. 4. The fitting portion 42A illustrated in FIG. 4 positions the antenna fixing portions 411 such that the receiving antennas 51 are positioned at appropriate positions relatively to the subject 2A having obese build. In this state, the string-like members 412Kd are, as illustrated in FIG. 23, in a straightened state.

Like in this third embodiment, the interlinking portion may have any configuration with a member that variably interlinks relative positions of the plural antenna fixing portions 411, and the interlinking portion may thus be configured without expanding and contracting portions. If the interlinking portion is configured without expanding and contracting portions, a configuration having the attachment portions 413G only at four corners like in the seventh modification illustrated in FIG. 14 is unable to be adopted, and thus each interlinked surface 412a needs to have one attachment portion 413 arranged thereon.

Fourth Embodiment

Figure 24:
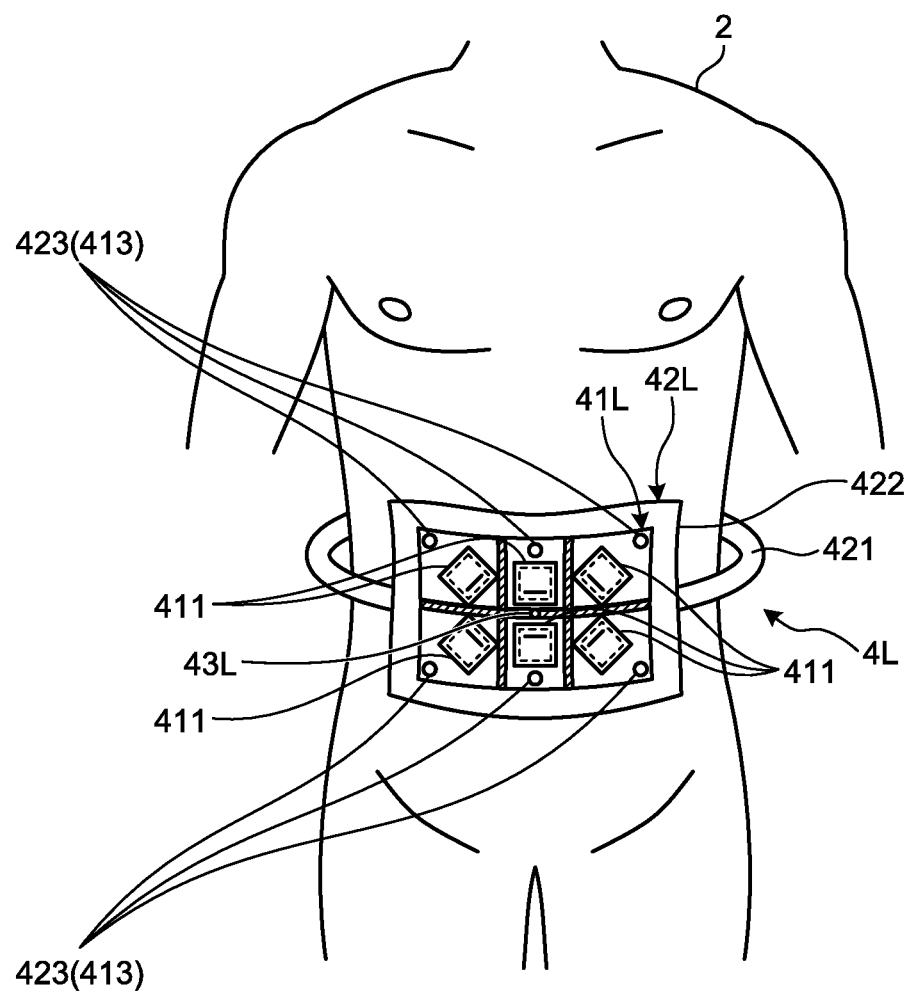
FIG. 24 is a schematic diagram illustrating a schematic configuration of an antenna holder according to a fourth embodiment.
Figure 25:
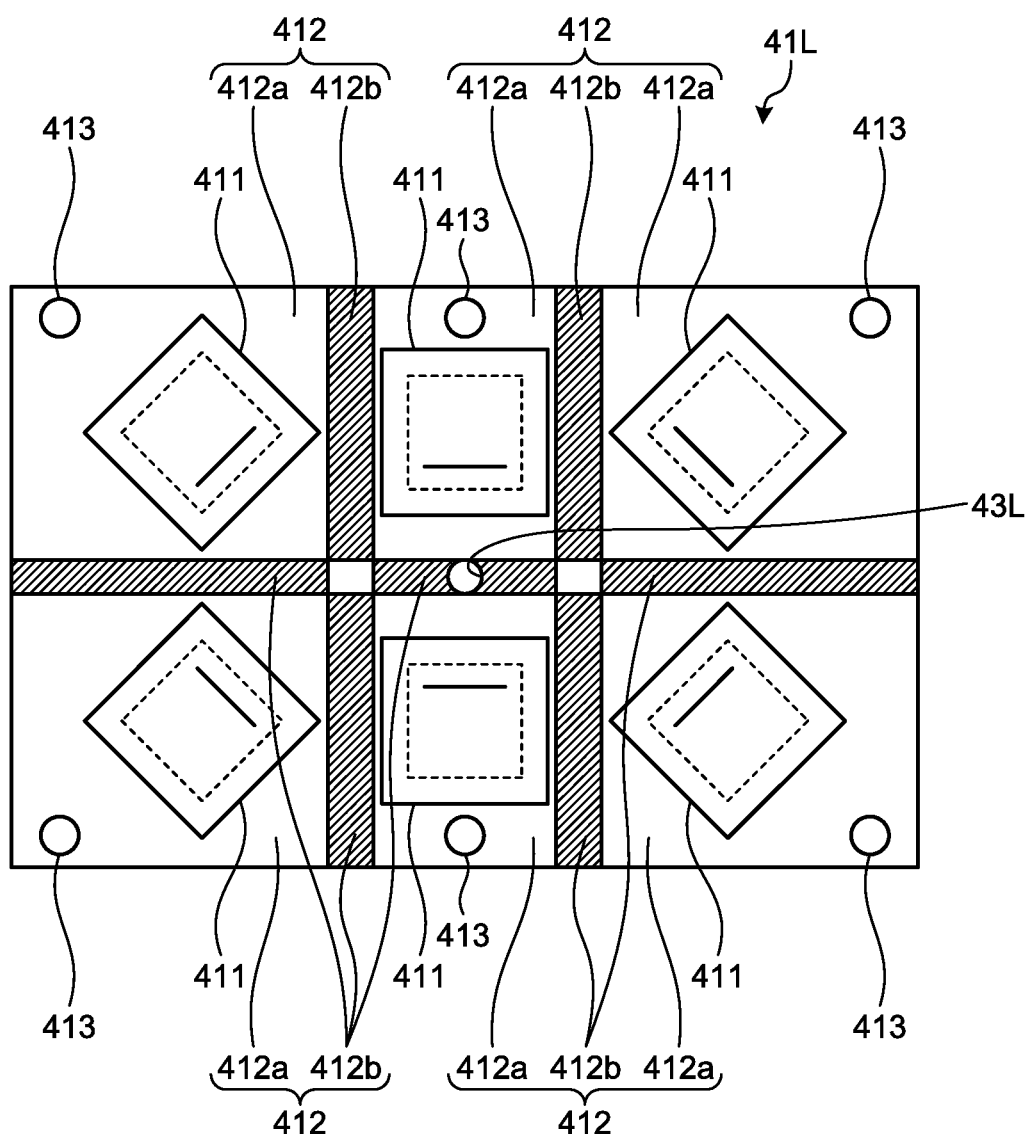
FIG. 25 is an enlarged view of an antenna attachment portion in FIG. 24.

FIG. 14 is a schematic diagram illustrating a schematic configuration of an antenna holder according to a fourth embodiment. FIG. 25 is an enlarged view of an antenna attachment portion. As illustrated in FIG. 24 and FIG. 25, an antenna attachment portion 41L and a fitting portion 42L of an antenna holder 4L according to the fourth embodiment has a reference hole 43L. The antenna holder 4L is fitted on the subject 2 by aligning the reference hole 43L with the navel of the subject 2, and the antenna holder 4L and the subject 2 are thereby able to be positioned appropriately.

Figure 26:
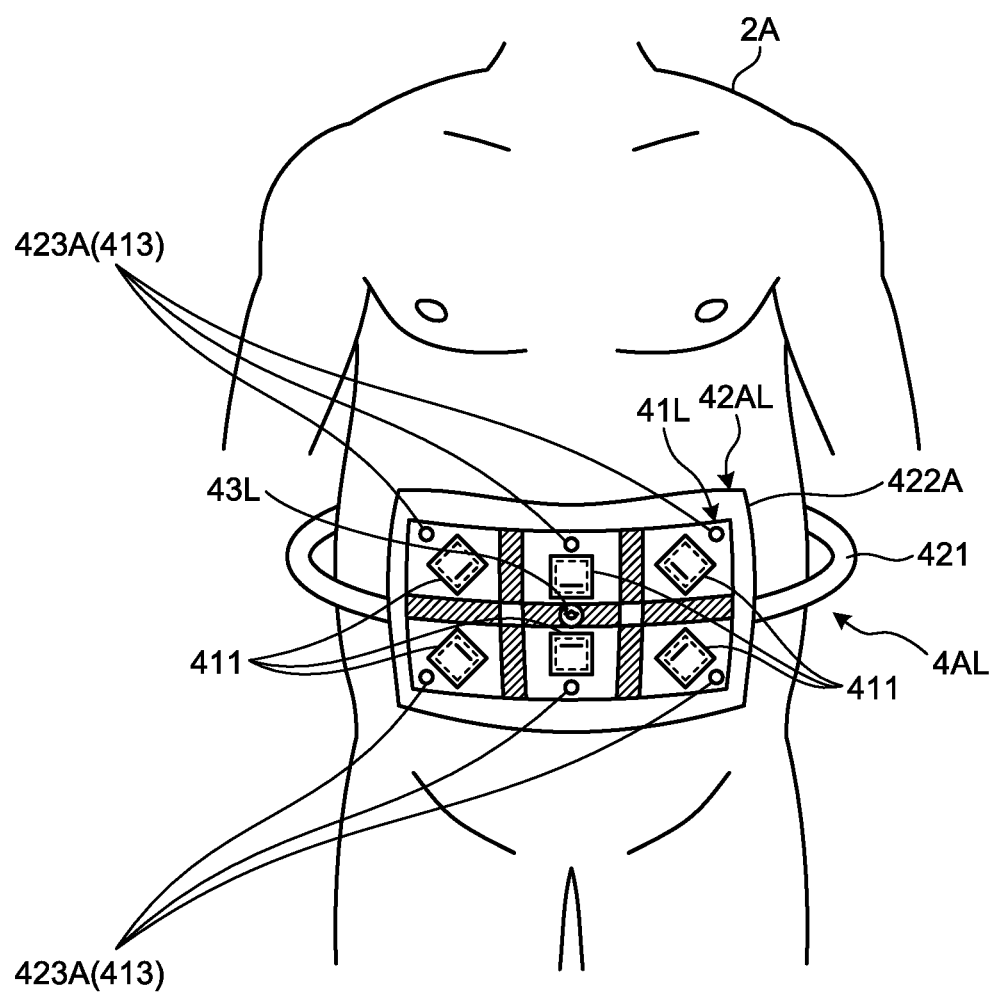
FIG. 26 is a diagram illustrating how the antenna holder according to the fourth embodiment is fitted on a subject having obese build.
Figure 27:
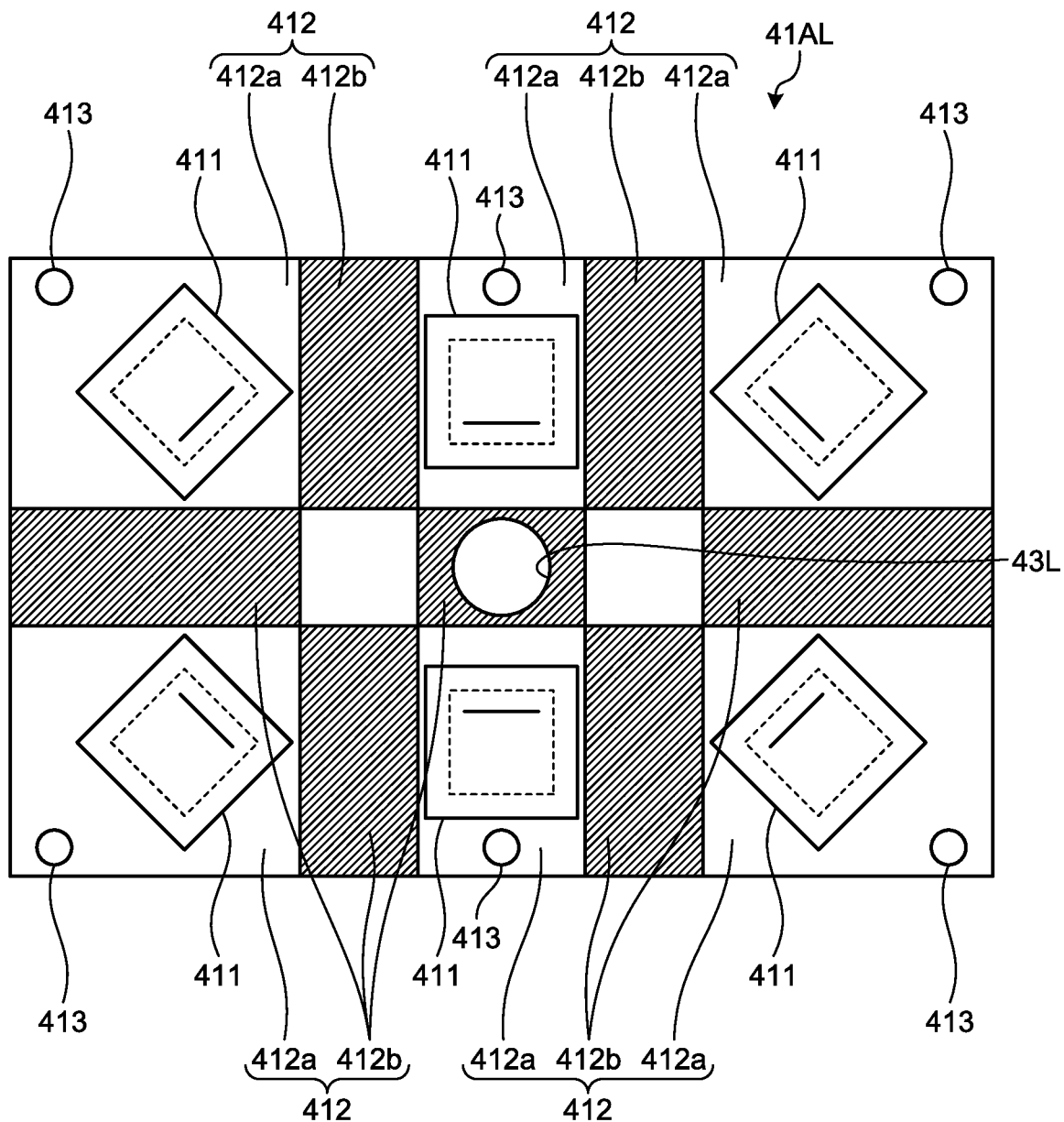
FIG. 27 is an enlarged view of an antenna attachment portion in FIG. 26.

FIG. 26 is a diagram illustrating how the antenna holder according to the fourth embodiment is fitted on a subject having obese build. FIG. 27 is an enlarged view of the antenna attachment portion. As illustrated in FIG. 26 and FIG. 27, when the antenna attachment portion 41L has been attached to a fitting portion 42AL suitable for the subject 2A having obese build also, an antenna holder 4AL and the subject 2A are able to be positioned appropriately by fitting of the antenna holder 4AL on the subject 2A through alignment of the reference hole 43L with the navel of the subject 2A.

Fifth Embodiment

Figure 28:
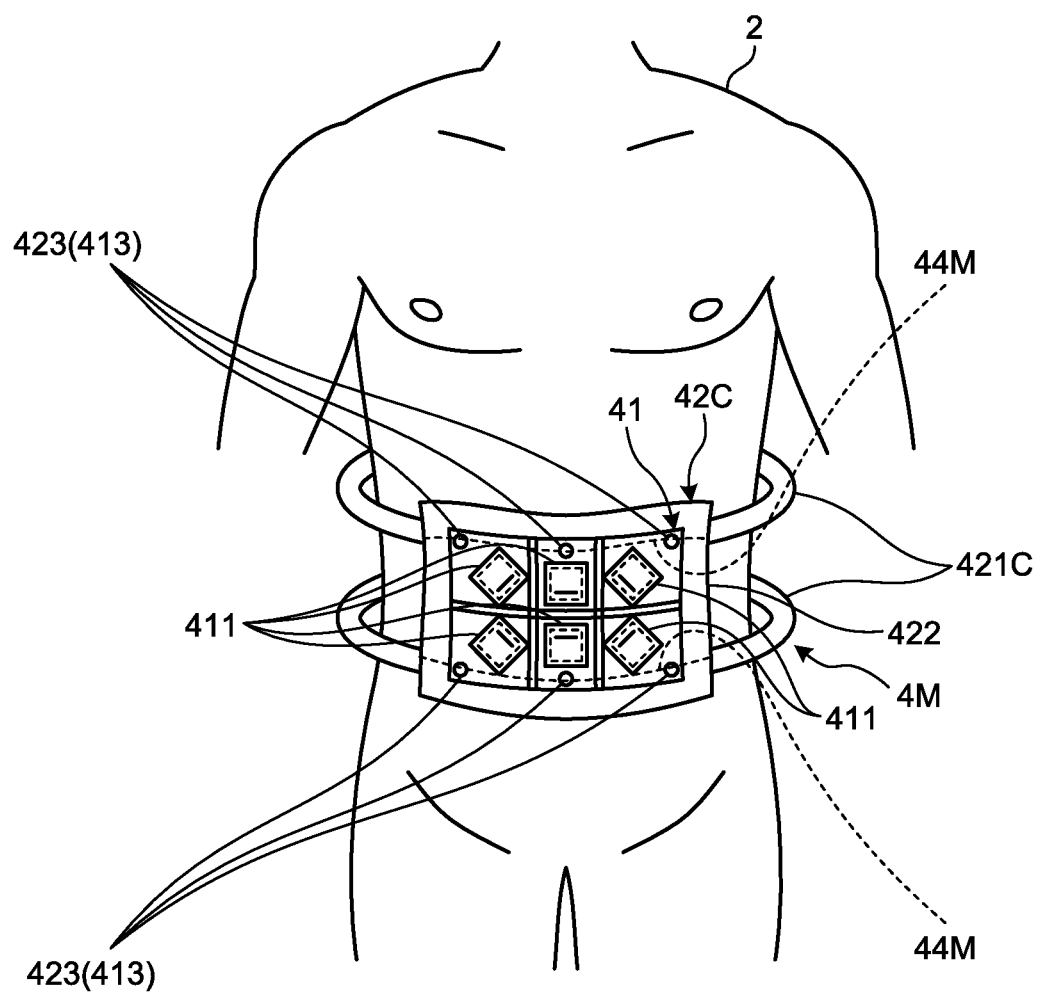
FIG. 28 is a schematic diagram illustrating a schematic configuration of an antenna holder according to a fifth embodiment.
Figure 29:
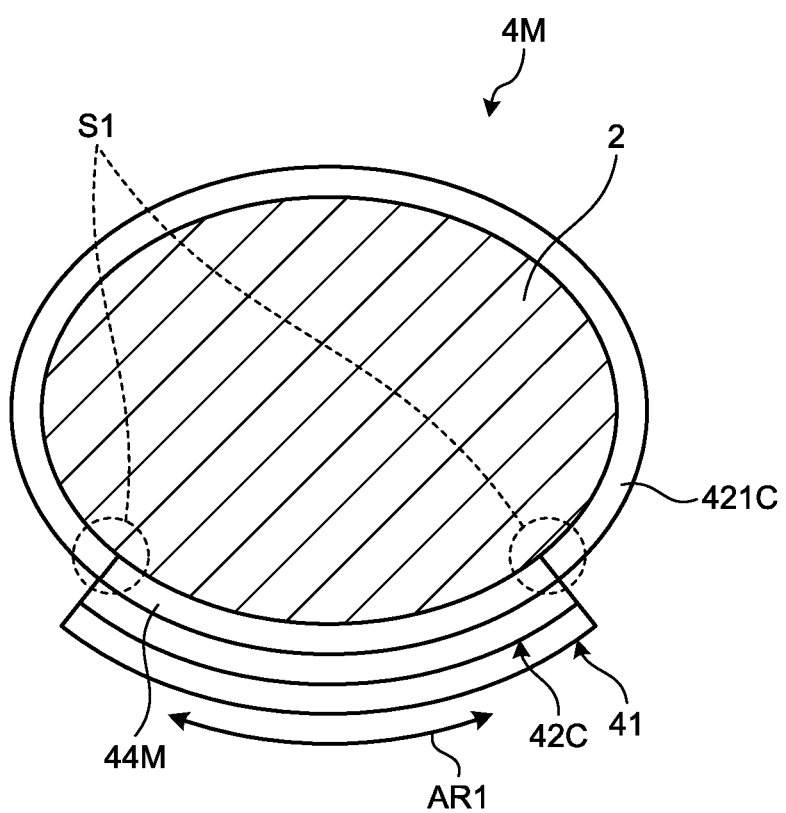
FIG. 29 is a diagram where FIG. 28 has been viewed from the top.

FIG. 28 is a schematic diagram illustrating a schematic configuration of an antenna holder according to a fifth embodiment. FIG. 29 is a diagram where FIG. 28 has been viewed from the top. As illustrated in FIG. 28 and FIG. 29, an antenna holder 4M according to the fifth embodiment has flexible members 44M arranged at both an upper end and a lower end that are more inside than the fitting portion 42C (toward the subject 2).

The flexible members 44M are each formed of shape memory alloy, an elastic wire, or the like, and are curved along the body surface of the subject 2. As a result, formation of gaps in regions S1 illustrated in FIG. 29 is prevented, the regions S1 being where gaps tend to be formed, and displacement of position of the antenna holder 4M in the waist circumference direction (an arrow AR1 in FIG. 29) is prevented, the position being relative to the subject 2.

Sixth Embodiment

Figure 30:
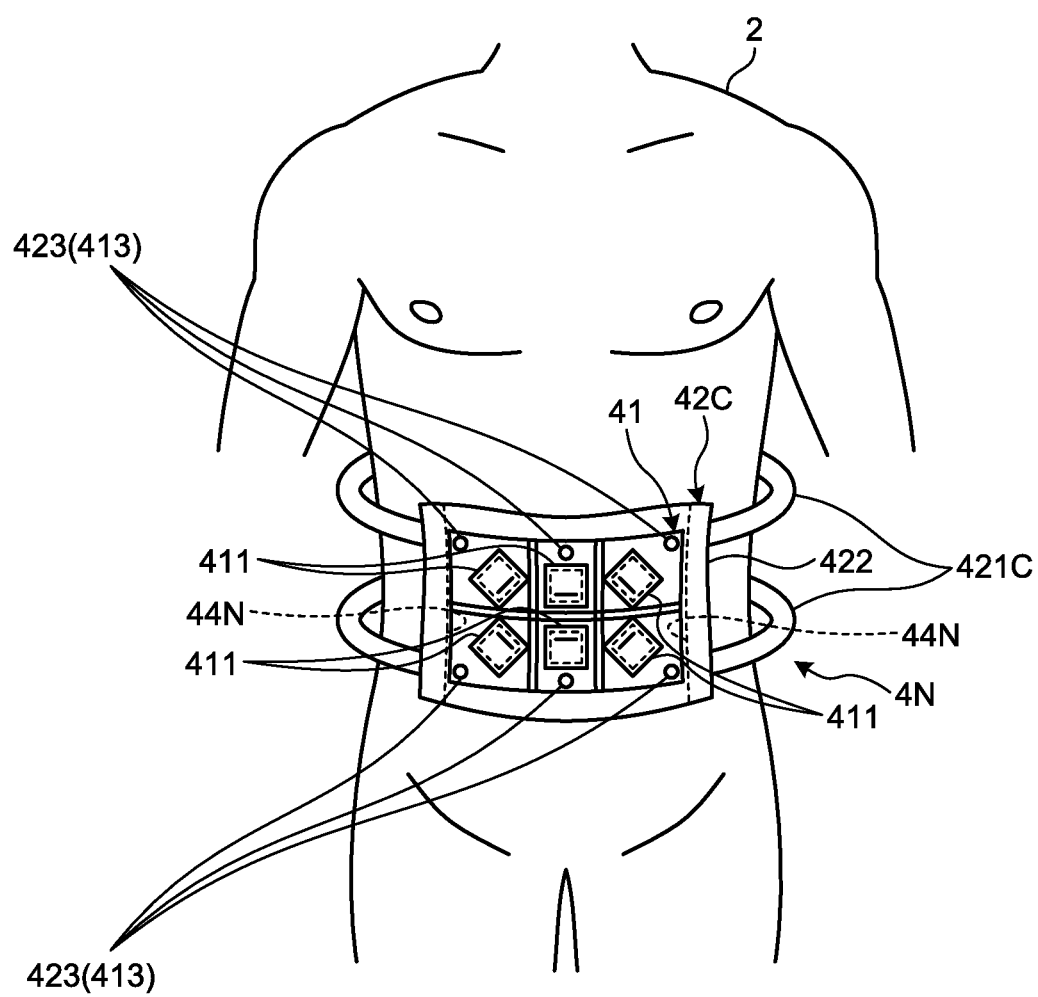
FIG. 30 is a schematic diagram illustrating a schematic configuration of an antenna holder according to a sixth embodiment.
Figure 31:
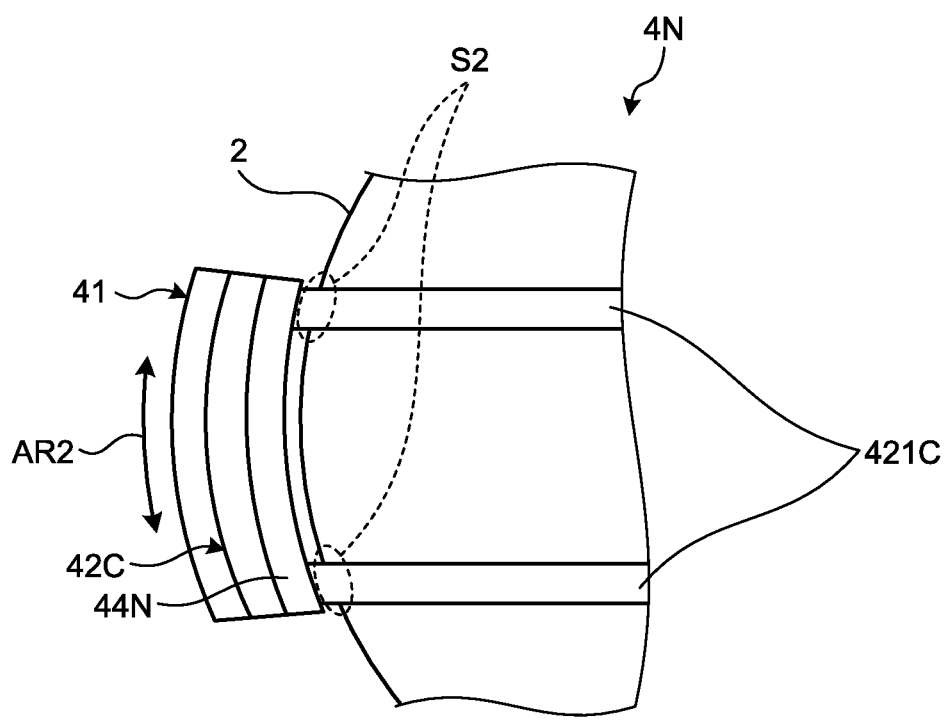
FIG. 31 is a diagram where FIG. 30 has been viewed from the side.

FIG. 30 is a schematic diagram illustrating a schematic configuration of an antenna holder according to a sixth embodiment. FIG. 31 is a diagram where FIG. 30 has been viewed from the side. As illustrated in FIG. 30 and FIG. 31, an antenna holder 4N according to the sixth embodiment has flexible members 44N arranged at both a left end and a right end that are more inside than the fitting portion 42C (toward the subject 2).

Similarly to the fifth embodiment, the flexible members 44N are each formed of shape memory alloy, an elastic wire, or the like, and are curved along the body surface of the subject 2. As a result, formation of gaps in regions S2 illustrated in FIG. 31 is prevented, the regions S2 being where gaps tend to be formed, and displacement of position of the antenna holder 4N in the body length direction (an arrow AR2 in FIG. 31) is prevented, the position being relative to the subject 2.

Seventh Embodiment

Figure 32:
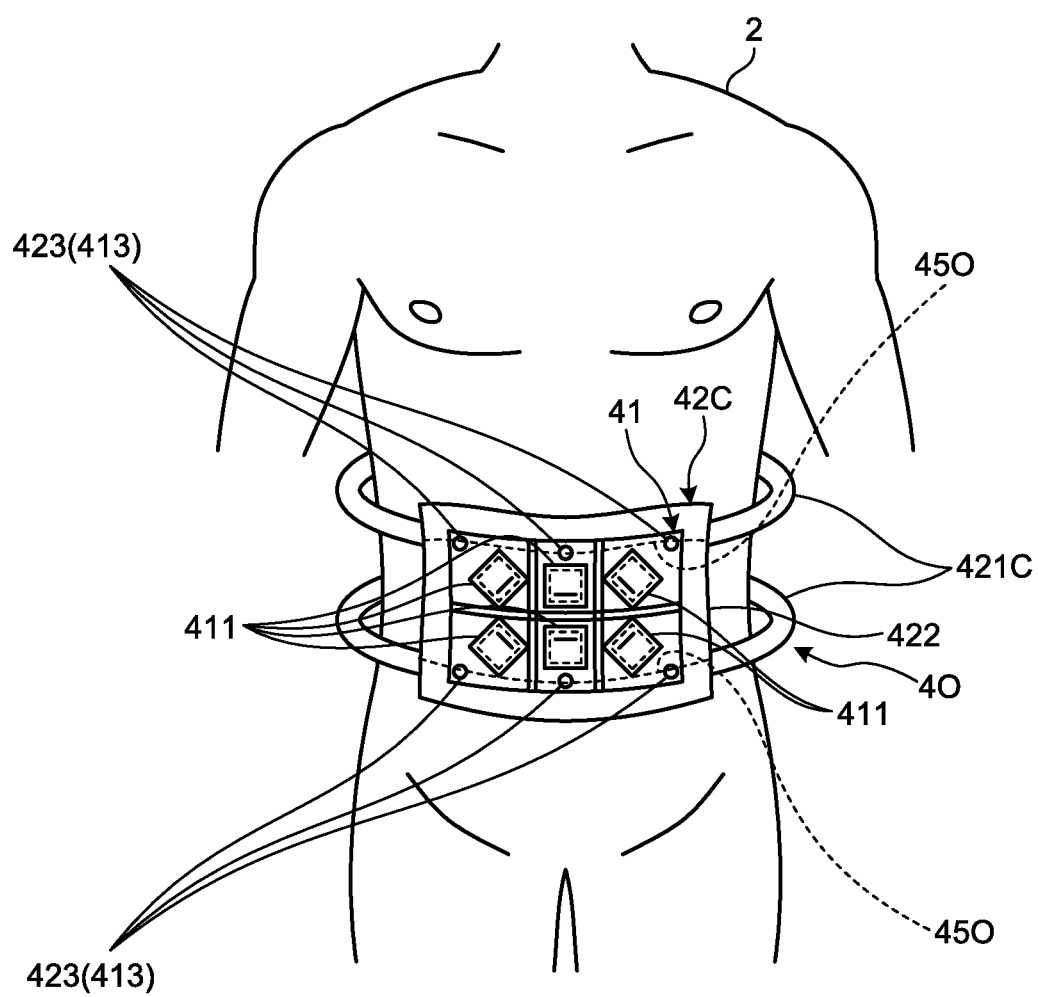
FIG. 32 is a schematic diagram illustrating a schematic configuration of an antenna holder according to a seventh embodiment.
Figure 33:
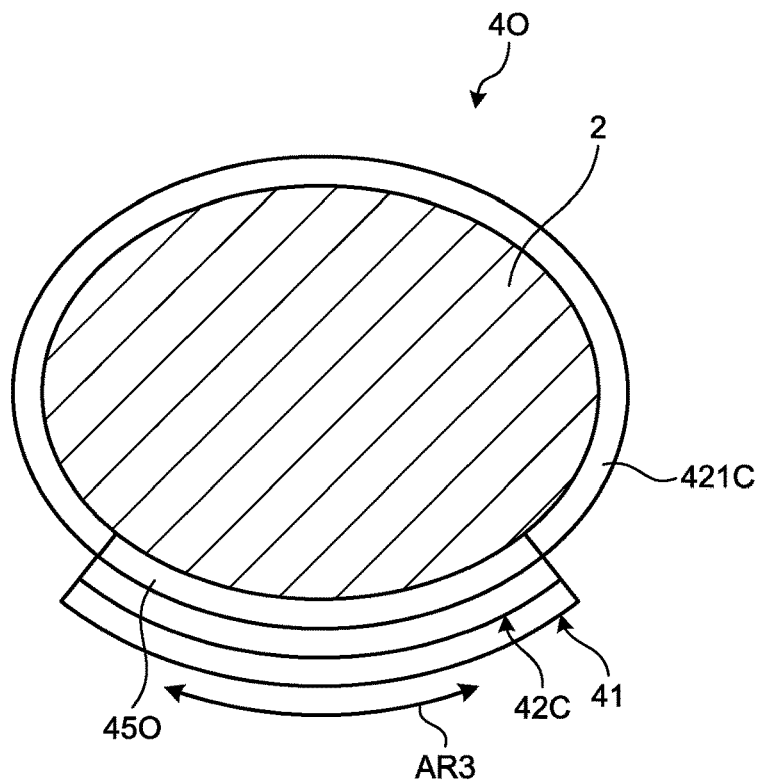
FIG. 33 is a diagram where FIG. 32 has been viewed from the top.

FIG. 32 is a schematic diagram illustrating a schematic configuration of an antenna holder according to a seventh embodiment. FIG. 33 is a diagram where FIG. 32 has been viewed from the top. As illustrated in FIG. 32 and FIG. 33, an antenna holder 4O according to the seventh embodiment has non-slip members 45O arranged at both an upper end and a lower end that are more inside than the fitting portion 42C (toward the subject 2). The non-slip members 45O are each formed of rubber or the like, and prevents position of the antenna holder 4O from being displaced in the waist circumference direction (an arrow AR3 in FIG. 33), the position being relative to the subject 2.

Configuration of Antenna Device

Figure 34:
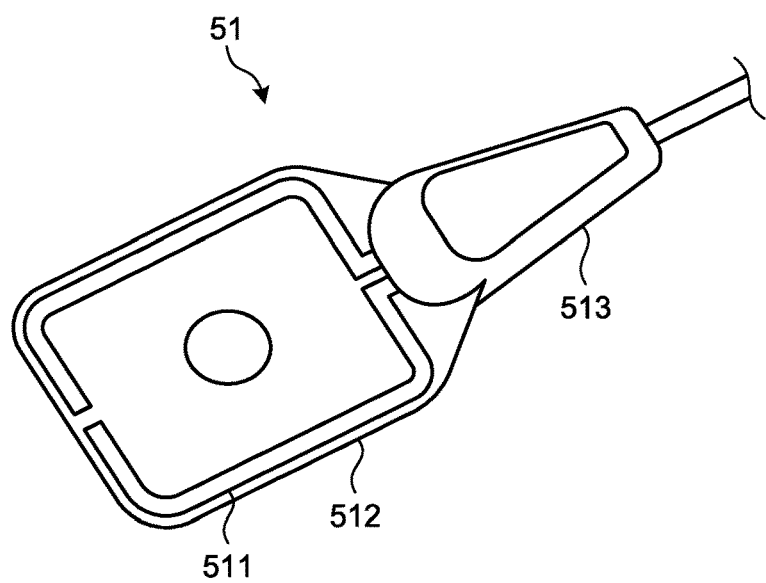
FIG. 34 is a perspective view of a receiving antenna.
Figure 35:
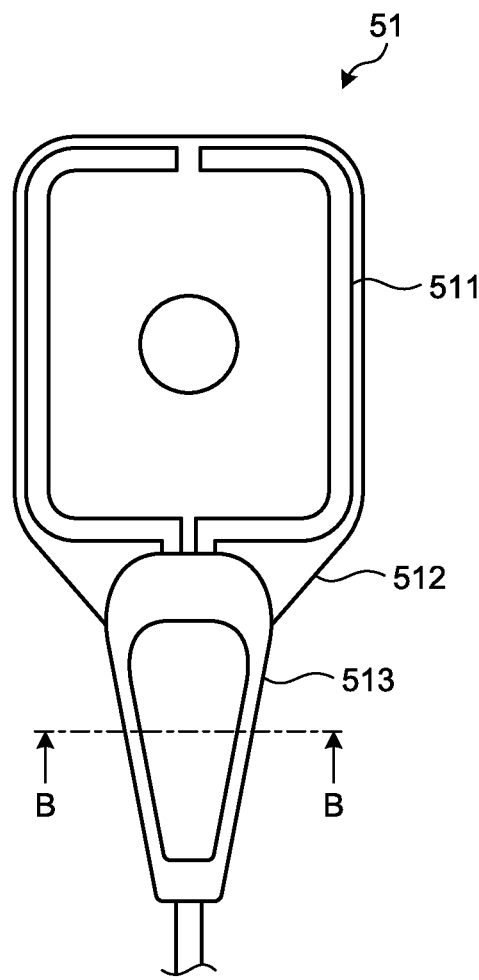
FIG. 35 is a top view of the receiving antenna.
Figure 36:
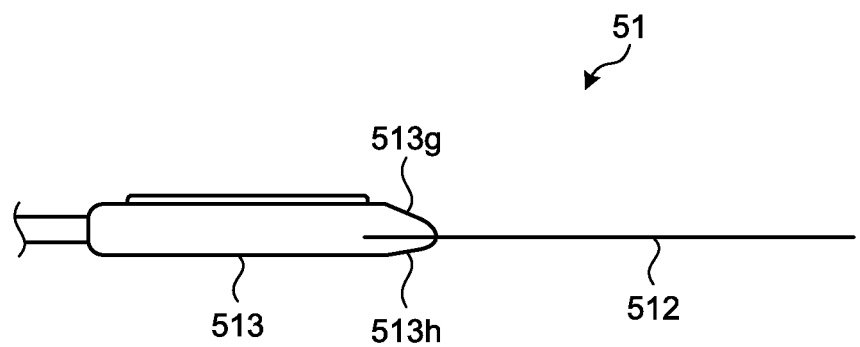
FIG. 36 is a side view of the receiving antenna.
Figure 37:
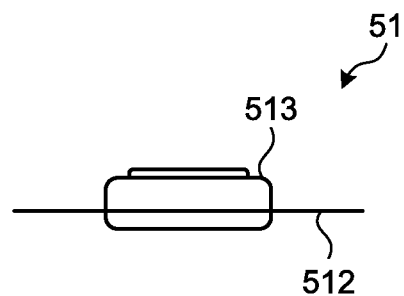
FIG. 37 is another side view of the receiving antenna.

A detailed configuration of the antenna device 5 will be described next. FIG. 34 is a perspective view of a receiving antenna. FIG. 35 is a top view of the receiving antenna. FIG. 36 and FIG. 37 are side views of the receiving antenna. As illustrated in FIG. 34 to FIG. 37, the receiving antennas 51 each have: an antenna line 511 that receives a wireless signal from the capsule endoscope device 3; a sheet portion 512 where the antenna line 511 is arranged and that is sheet-like; and a connecting portion 513 that connects the antenna line 511 and the antenna cables 53 together.

Figure 38:
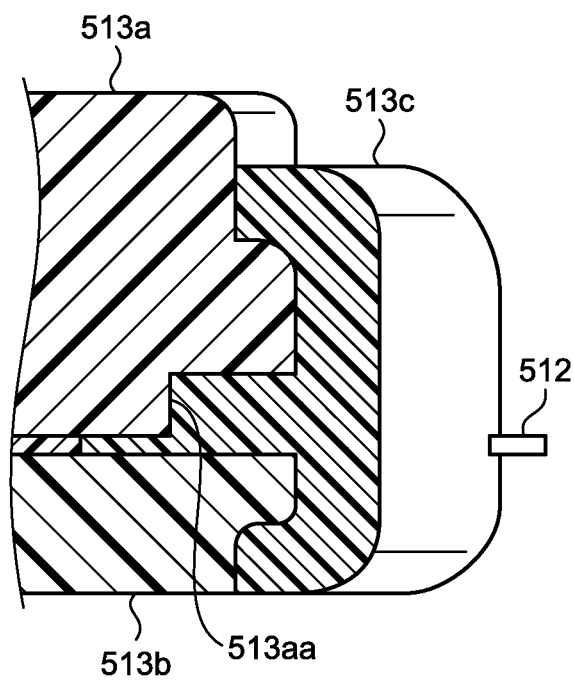
FIG. 38 is a sectional view corresponding to a B-B line in FIG. 35.

FIG. 38 is a sectional view corresponding to a B-B line in FIG. 35. As illustrated in FIG. 38, the connecting portion 513 has a rigid member 513a that covers an upper surface side of the connecting portion 513, a rigid member 513b that covers a lower surface side of the connecting portion 513, and a flexible member 513c that covers a side surface of the connecting portion 513. The rigid member 513a and the rigid member 513b are formed of, for example, rigid resin, and the flexible member 513c is formed of, for example, flexible resin.

The rigid member 513a has a concave portion 513aa formed therein, and when the rigid member 513a, the rigid member 513b, and the flexible member 513c are unitarily formed together, the flexible member 513c flows into the concave portion 513aa. As a result, force is applied to the connecting portion 513 from the top and from the bottom in FIG. 38, and the rigid member 513a and rigid member 513b are prevented from being separated from the flexible member 513c.

Figure 39:
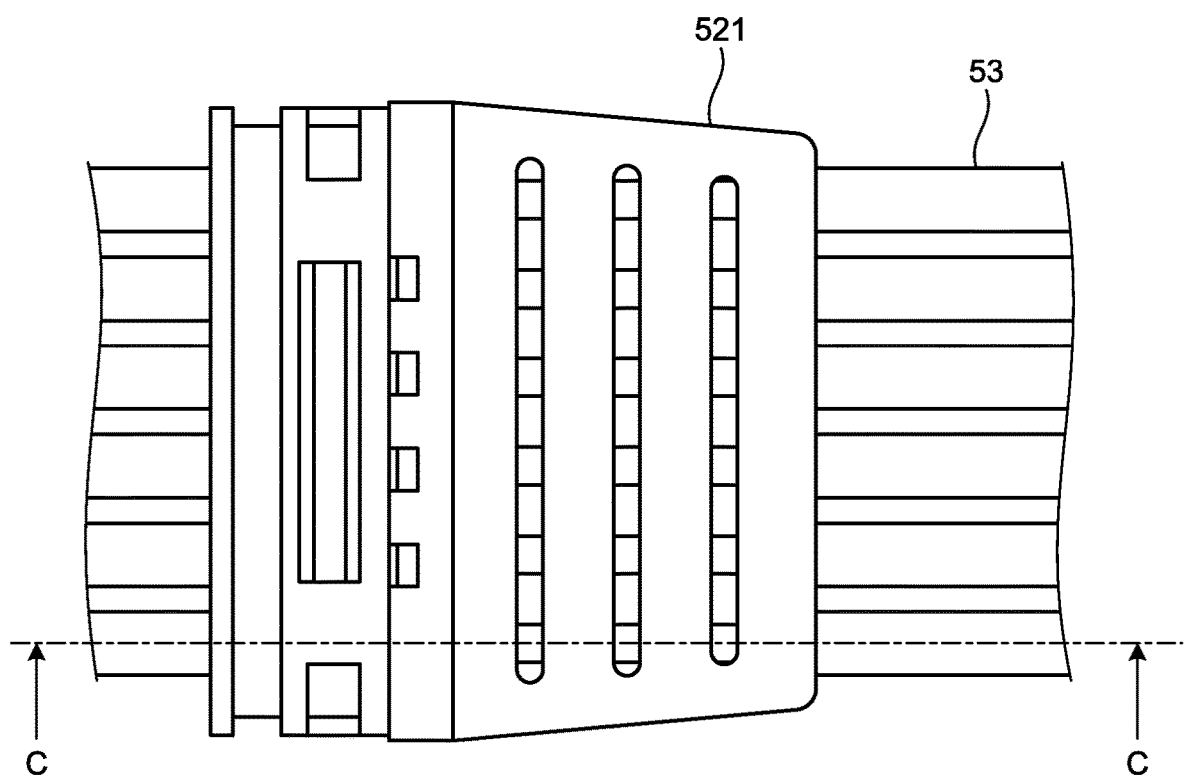
FIG. 39 is an enlarged view of a connecting portion of a connector portion illustrated in FIG. 6.
Figure 40:
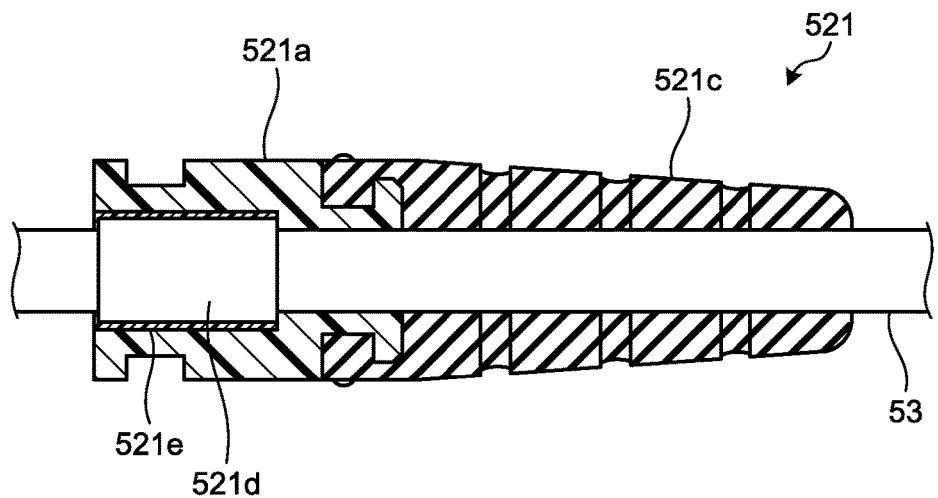
FIG. 40 is a partial cutaway diagram corresponding to a C-C line in FIG. 39.

FIG. 39 is an enlarged view of a connecting portion (a connecting portion 521) of a connector portion illustrated in FIG. 6. FIG. 40 is a partial cutaway diagram corresponding to a C-C line in FIG. 39. As illustrated in FIG. 40, the connecting portion 521 connecting a connector portion 52 and the antenna cables 53 together has: a rigid member 521a covering a part of the connecting portion 521; a flexible member 521c connected to a proximal end of the connecting portion 521 (toward the antenna cables 53); a swaged member 521d having the antenna cables 53 inserted therethrough; and a flexible member 521e filled around the swaged member 521d. The rigid member 521a is formed of, for example, rigid resin, and the flexible member 521c and the flexible member 521e are formed of, for example, flexible resin.

The swaged member 521d is, for example, a member that is tube-like and formed of metal, and is fixed to the antenna cables 53 by being swaged in the state where the antenna cables 53 have been inserted therethrough. As illustrated in FIG. 40, by the arrangement of the swaged member 521d in a gap in the rigid member 521a and filling of the flexible member 521e around the swaged member 521d, the antenna cables 53 are prevented from coming off from the connector portion 52.

Figure 41:
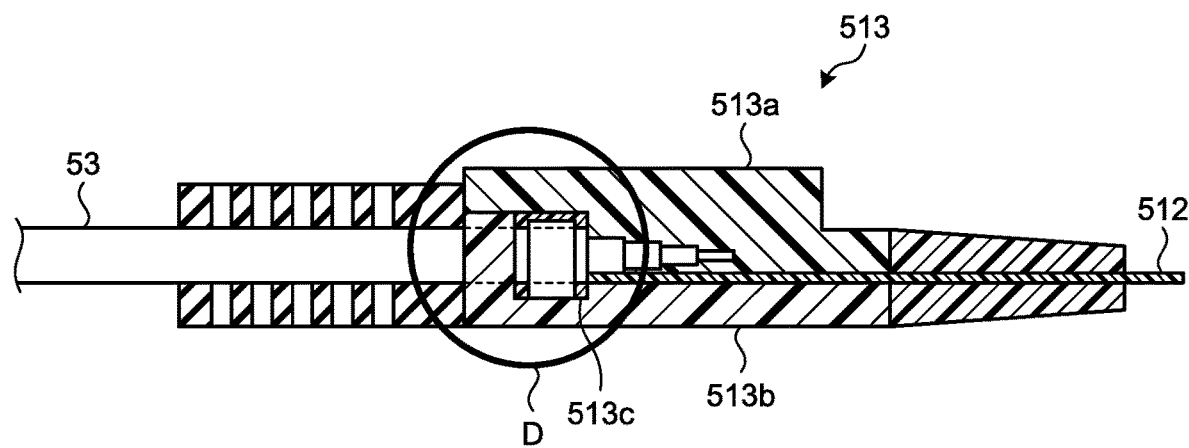
FIG. 41 is a partial cutaway diagram of a connecting portion of the receiving antenna.
Figure 42:
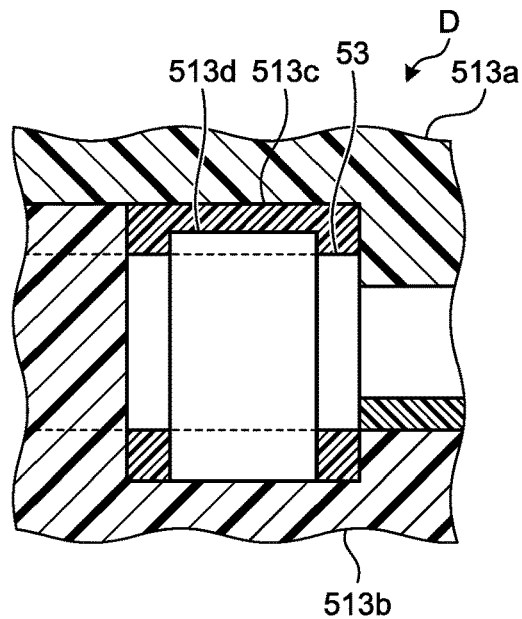
FIG. 42 is an enlarged view of a region D illustrated in FIG. 41.

FIG. 41 is a partial cutaway diagram of the connecting portion (the connecting portion 513) of a receiving antenna. FIG. 42 is an enlarged view of a region D illustrated in FIG.

41. As illustrated in FIG. 42, the connecting portion 513 has a swaged member 513d having the antenna cable 53 inserted therethrough. The swaged member 513d is, for example, a member that is tube-like and formed of metal, and is fixed to the antenna cable 53 by being swaged in the state where the antenna cable 53 has been inserted therethrough. By the arrangement of the swaged member 513d in the gap between the rigid member 513a and the rigid member 513b and the filling of the flexible member 513c around the swaged member 513d, the antenna cable 53 is prevented from coming off from the connecting portion 513.

Figure 43:
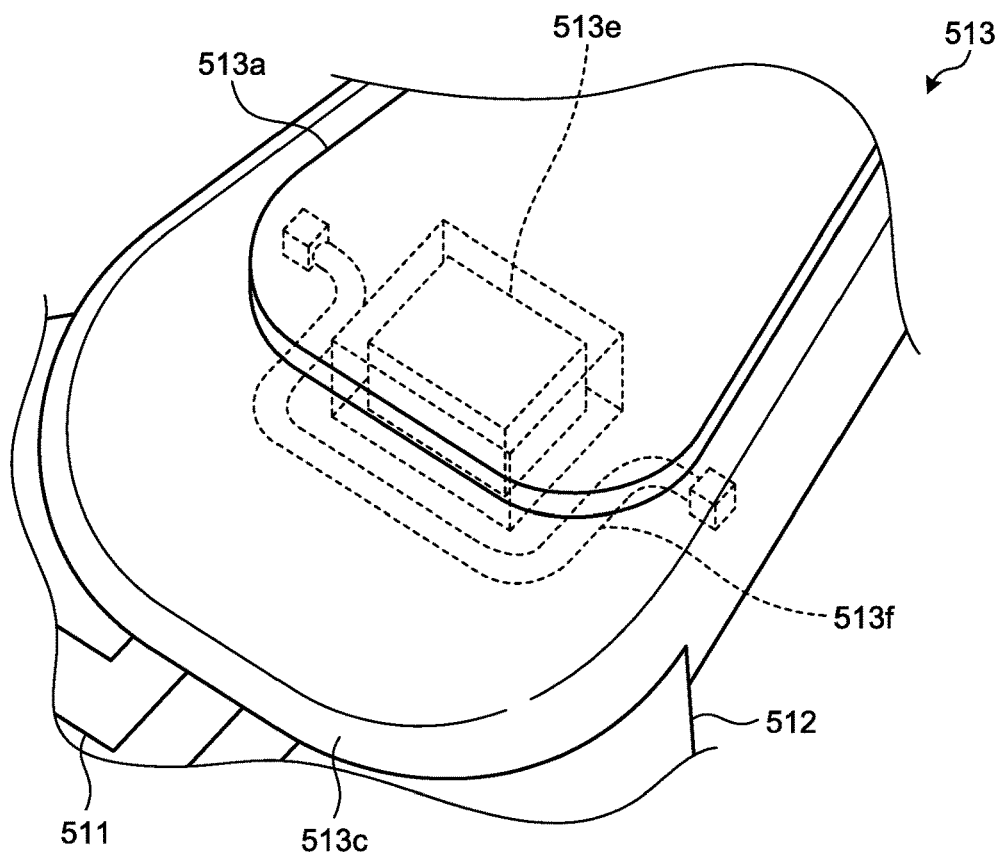
FIG. 43 is a partial perspective view of the connecting portion of the receiving antenna.
Figure 44:
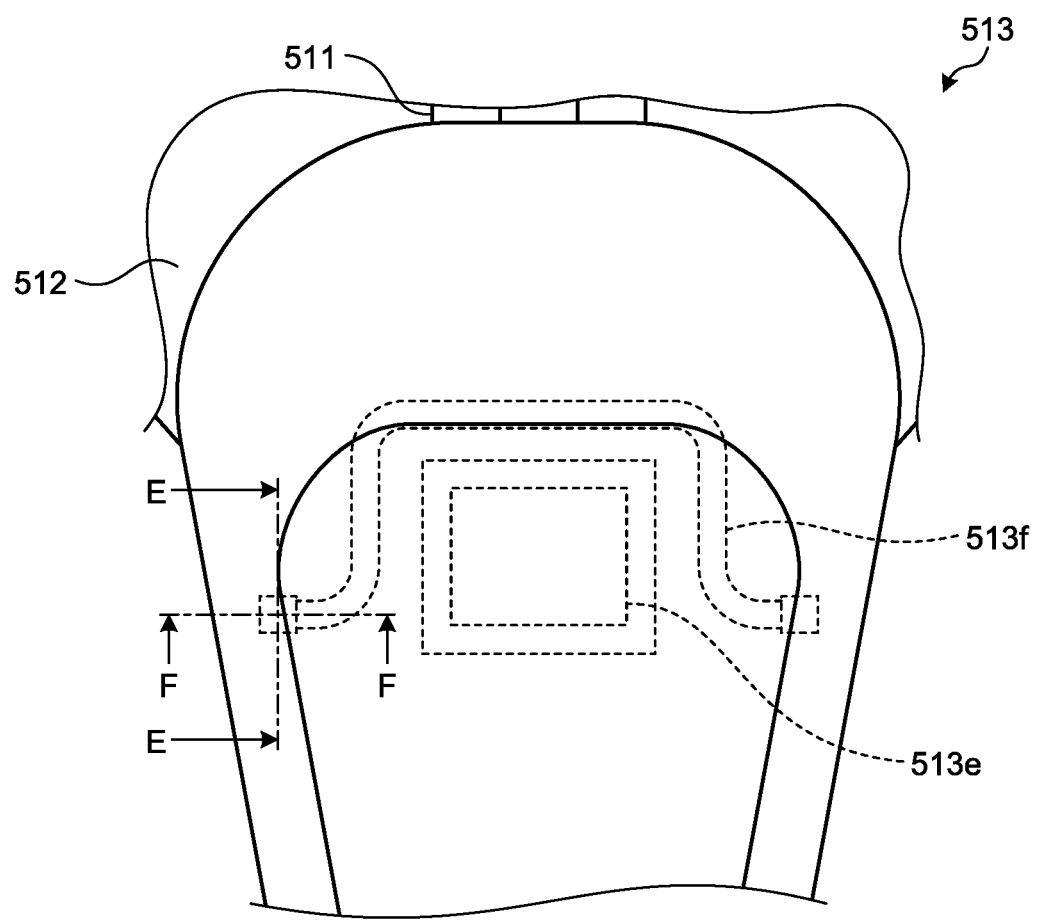
FIG. 44 is a partial top view of the connecting portion of the receiving antenna.

FIG. 43 is a partial perspective view of the connecting portion (the connecting portion 513) of the receiving antenna. FIG. 44 is a partial top view of the connecting portion (the connecting portion 513) of the receiving antenna. As illustrated in FIG. 43 and FIG. 44, an electronic component 513e electrically connected to the antenna line 511 is stored inside the connecting portion 513. Packing 513f is arranged at a distal end side (toward the antenna line 511) of the electronic component 513e. The packing 513f is formed of a member made of silicone, rubber, or the like, and prevents liquid that has entered from a gap between the sheet portion 512 and the flexible member 513c from reaching the electronic component 513e.

Figure 45:
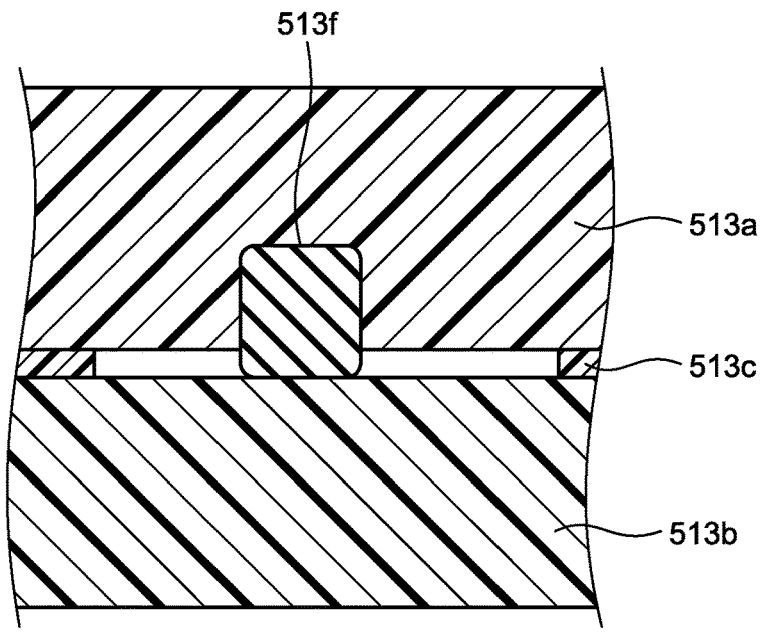
FIG. 45 is a sectional view corresponding to an E-E line in FIG. 44.
Figure 46:
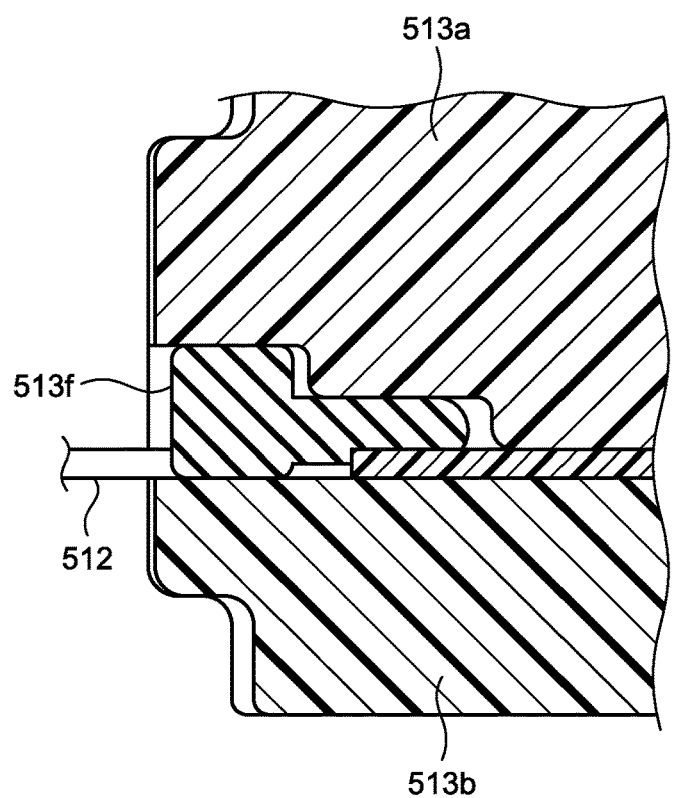
FIG. 46 is a sectional view corresponding to an F-F line in FIG. 44.

FIG. 45 is a sectional view corresponding to an E-E line in FIG. 44. FIG. 46 is a sectional view corresponding to an F-F line in FIG. 44. As illustrated in FIG. 45 and FIG. 46, end portions of the packing 513f are formed quadrangularly, and are fitted in concave portions provided in the rigid member 513a. By the packing 513f being fitted into the concave portions, liquid is prevented from going therein from the end portions of the packing 513f.

As illustrated in FIG. 36, the connecting portion 513 has an inclined portion 513g and an inclined portion 513h respectively formed at the top and bottom of the connecting portion 513, the top and bottom being toward the sheet portion 512. As a result, difference in level of the sheet portion 512 from the connecting portion 513 is reduced, and when the receiving antenna 51 is bent, application of a large load on a boundary between the sheet portion 512 and the connecting portion 513 is prevented.

Figure 47:
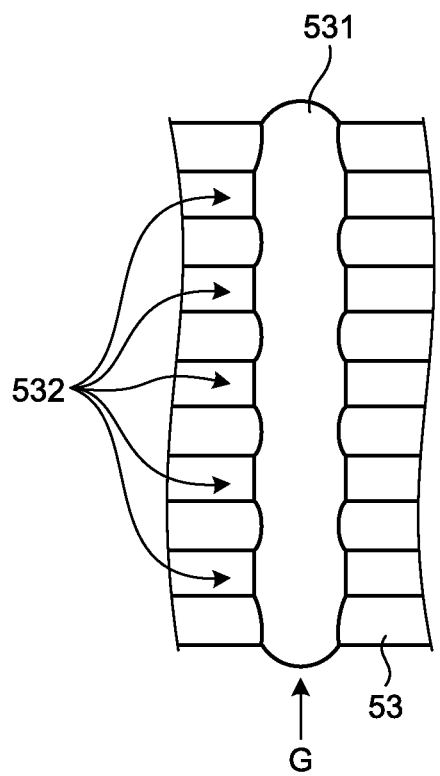
FIG. 47 is an enlarged view of a cable binding portion illustrated in FIG. 6.
Figure 48:
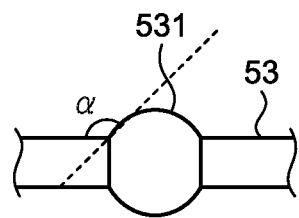
FIG. 48 is a diagram viewed in a direction of a G-arrow in FIG. 47.

FIG. 47 is an enlarged view of a cable binding portion illustrated in FIG. 6. FIG. 48 is a diagram viewed in a direction of a G-arrow in FIG. 47. As illustrated in FIG. 47, a cable binding portion 531 binds the plural antenna cables 53 such that gaps 532 are formed between adjacent ones of the antenna cables 53. As illustrated in FIG. 48, the cable binding portion 531 is spherical when viewed from the side. As a result, a cleaning tool, such as a brush, is easy to be moved into the gaps 532, and cleanability for uncleanness accumulated in the gaps 532 is improved. However, the cable binding portion 531 is not necessarily spherical as long as the cable binding portion 531 has a shape enabling the cleanability to be improved, and an angle α (see FIG. 48) formed between a direction, in which the antenna cable 53 extends, and a direction, in which the cable binding portion 531 protrudes with respect to the antenna cable 53 just needs to be at least obtuse.

According to an embodiment, an antenna holder, to which receiving antennas are able to be attached at appropriate positions according to build of a subject, is able to be realized.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An antenna holder comprising:
   an antenna attachment portion attached with a plurality of receiving antennas configured to receive wireless signals transmitted from a medical device introduced into a subject; and
   a fitting portion where the antenna attachment portion is detachably attached and that is fitted on the subject, wherein
   the antenna attachment portion includes:
      a plurality of antenna fixing portions where at least one of positions of the plurality of receiving antennas is fixed;
      an interlinking portion configured to variably interlink relative positions of the plurality of antenna fixing portions; and
      a first attachment portion attached to the fitting portion, and
   the fitting portion includes:
      a second attachment portion where the first attachment portion is detachably attached, the second attachment portion being configured to determine positions of the plurality of antenna fixing portions upon fitting of the plurality of antenna fixing portions on the subject, according to a build of the subject.

2. The antenna holder according to claim 1, comprising:
   a plurality of the fitting portions each having a size according to the build of the subject, wherein
   a plurality of the second attachment portions included in each of the plurality of the fitting portions are a plurality of position fixing portions configured to fix positions of the plurality of antenna fixing portions upon fitting of the plurality of antenna fixing portions on the subject, in a state where the positions have been positioned at positions that have been determined beforehand according to the build of the subject and that are different from one another.

3. The antenna holder according to claim 1, wherein the second attachment portion has a plurality of position fixing portions configured to fix positions of the plurality of antenna fixing portions upon fixing of the plurality of antenna fixing portions on the subject, in a state where the positions have been positioned at positions that have been determined beforehand according to the build of the subject and that are different from one another.

4. The antenna holder according to claim 1, wherein the interlinking portion is attachable to and detachable from the antenna fixing portions.

5. The antenna holder according to claim 1, wherein the fitting portion comprises:
   a surface where the second attachment portion is arranged; and
   a surface covering the antenna attachment portion.

6. The antenna holder according to claim 1, wherein the second attachment portion is configured to position the plurality of antenna fixing portions upon fitting of the plurality of antenna fixing portions on the subject, at a plurality of positions that have been determined beforehand according to the build of the subject and that are different from one another, in at least one of a waist circumference direction or a body length direction of the subject.

7. The antenna holder according to claim 3, wherein the plurality of position fixing portions differ from one another in at least one of color or shape.

8. The antenna holder according to claim 1, wherein the interlinking portion includes an expanding and contracting portion configured to expand and contract in at least one of a waist circumference direction or a body length direction of the subject.

9. The antenna holder according to claim 2, wherein an interval in a waist circumference direction of the plurality of the second attachment portions of the fitting portion fitted on a subject having a normal build is smaller than an interval in a waist circumference direction of the plurality of the second attachment portions of the fitting portion fitted on a subject having a larger waist circumference than that of the normal build.

10. The antenna holder according to claim 3, wherein an interval in a waist circumference direction of the plurality of the second attachment portions for attachment of the antenna attachment portion to a subject having a normal build is smaller than an interval in a waist circumference direction of the plurality of the second attachment portions for attachment of the antenna attachment portion to a subject having a larger waist circumference than that of the normal build.

11. The antenna holder according to claim 2, wherein an interval in a body length direction of the plurality of the second attachment portions of the fitting portion fitted on a subject having a normal build is smaller than an interval in a body length direction of the plurality of the second attachment portions of the fitting portion fitted on a subject having a longer body length than that of the normal build.

12. The antenna holder according to claim 3, wherein an interval in a body length direction of the plurality of the second attachment portions for attachment of the antenna attachment portion to a subject having a normal build is smaller than an interval in a body length direction of the plurality of the second attachment portions for attachment of the antenna attachment portion to a subject having a longer body length than that of the normal build.

13. An antenna attachment portion attached with a plurality of receiving antennas configured to receive wireless signals transmitted from a medical device introduced into a subject and detachably to a fitting portion that is fitted on the subject, the antenna attachment portion comprising:
   a plurality of antenna fixing portions where at least one of positions of the plurality of receiving antennas is fixed;
   an interlinking portion configured to variably interlink relative positions of the plurality of antenna fixing portions; and
   a first attachment portion attached to the fitting portion.

* * * * *